US012059507B2

(12) United States Patent
Braschler et al.

(10) Patent No.: US 12,059,507 B2
(45) Date of Patent: Aug. 13, 2024

(54) COMPOSITION COMPRISING A CROSS-LINKED POLYOL

(71) Applicant: Volumina Medical SA, Epalinges (CH)

(72) Inventors: Thomas Braschler, Epalinges (CH); Amelie Beduer, Epalinges (CH); Patrick Burch, Epalinges (CH)

(73) Assignee: Volumina Medical SA, Epalinges (CH)

( * ) Notice: Subject to any disclaimer, the term of this patent is extended or adjusted under 35 U.S.C. 154(b) by 424 days.

(21) Appl. No.: 17/600,682

(22) PCT Filed: Apr. 2, 2019

(86) PCT No.: PCT/CH2019/000009
§ 371 (c)(1),
(2) Date: Oct. 1, 2021

(87) PCT Pub. No.: WO2020/198888
PCT Pub. Date: Oct. 8, 2020

(65) Prior Publication Data
US 2022/0160936 A1    May 26, 2022

(51) Int. Cl.
*A61L 27/20*    (2006.01)
*A61L 27/50*    (2006.01)

(52) U.S. Cl.
CPC ............... *A61L 27/20* (2013.01); *A61L 27/50* (2013.01); *A61L 2430/34* (2013.01)

(58) Field of Classification Search
CPC .......... A61L 27/20; A61L 27/50; A61L 27/52; A61L 2430/34
See application file for complete search history.

(56) References Cited

U.S. PATENT DOCUMENTS 5,629,191 A    5/1997    Cahn
5,632,774 A    5/1997    Babian
(Continued)

FOREIGN PATENT DOCUMENTS

WO    2016/011387    1/2016
WO    2016011387    1/2016
(Continued)

OTHER PUBLICATIONS

Beduer, et al., "A Compressible Scaffold for Minimally Invasive Delivery of Large Intact Neuronal Networks", Advanced Healthcare Materials, 4(2): 301-312 (2015).
(Continued)

*Primary Examiner* — Carlos A Azpuru
(74) *Attorney, Agent, or Firm* — PABST PATENT GROUP LLP

(57) ABSTRACT

The composition comprises a polyol crosslinked with a) a multifunctional epoxide; or b) an epihalohydrin; or c) a molecule or crosslinker mixture comprising multiple epihalohydrin and/or epoxide groups or molecules. The composition has a number $N_1$ of effective ether crosslinks per crosslinker molecule as calculated by subtracting 1 from the average number of distinct polyol repeat units bound per crosslinker molecule. The remaining reactive groups on the crosslinker are ineffective in crosslinking and provide a number $N_2$ of pendant groups per crosslinker molecule. Among the $N_2$ groups per crosslinker there are $N_3$ groups per crosslinker that are unreacted or otherwise retain reactivity against nucleophiles. The relationship between $N_1$ and $N_2$ is: $N_1 > 0.35 (N_1 + N_2)$.

25 Claims, 16 Drawing Sheets

(56) References Cited

U.S. PATENT DOCUMENTS

| | | | |
|---|---|---|---|
| 7,993,679 | B2 | 8/2011 | Ingram |
| 2005/0186240 | A1 | 8/2005 | Ringeisen |
| 2009/0326654 | A1 | 12/2009 | Powell |
| 2011/0293722 | A1 | 12/2011 | Kaully |
| 2014/0308362 | A1 | 10/2014 | Bellas |
| 2015/0057368 | A1 | 2/2015 | Connelly |
| 2016/0101213 | A1 | 4/2016 | Seyedin |
| 2017/0196818 | A1 | 7/2017 | Shin |
| 2019/0062461 | A1* | 2/2019 | Karlsson ............ C08J 3/075 |

FOREIGN PATENT DOCUMENTS

| | | |
|---|---|---|
| WO | 2017/029633 | 2/2017 |
| WO | 2017029633 | 2/2017 |

OTHER PUBLICATIONS

Bencherif, et al. "Injectable preformed scaffolds with shape-memory properties", PNAS, 109(48): 19590-19595 (2012).

Cascone, et al., "Hydrogel-based commercial products for biomedical applications: A review", International Journal of Pharmaceutics, 118803 (2001).

Claro, et al., "Applicability and safety of autologous fat for reconstruction of the breast", British Journal of Surgery, 99(6): 768-780, (2012).

Coleman, et al., "Fat Grafting to the Breast Revisited: Safety and Efficacy", Plastic and Reconstructive Surgery, 119(3): 775-785 (2007).

Definition of "polysaccharide", Oxford English Dictionary. Accessed online on May 21, 2021 at www.oed.com. (Year: 2021).

Findlay, et al., "Tissue-Engineered Breast Reconstruction: Bridging the Gap toward Large-Volume Tissue Engineering in Humans", Plastic and Reconstructive Surgery, 128(6):1206-1215 (2011).

Gun'ko, et al., "Cryogels: Morphological, structural and adsorption characterisation", Advances in Colloid and Interface Science, 187-188:1-46 (2013).

Gundersen, et al. "Surface Structure and Wetting Characteristics of Collembola Cuticles", PloS One, 9(2):1-11 (2014).

Howes, et al., "Autologous Fat Grafting for Whole Breast Reconstruction", Plastic Reconstruction Surgery Global Open, 2(3): e124 (2014).

International Preliminary Report on Patentability for PCT/CH2019/000009 dated Jul. 5, 2021.

International Search Report for PCT application PCT/CH2018/000041 dated Dec. 17, 2018.

International Search report for PCT application PCT/CH2019/000009 dated Jan. 27, 2020.

Kuniak, et al., "Study of the Crosslinking Reaction between Epichlorohydrin and Starch", Starch: international journal for the investigation, processing and use of carbohydrates and their derivatives, 24(4): 110-116 (1972).

Maiti, et al., "In vivo measurement of skin surface strain and sub-surface layer deformation induced by natural tissue stretching", J. of the Mech. Behavior of Biomed. Mater., 62:556-569 (2016).

Mao, et al., "Facial Reconstruction by Biosurgery: Cell Transplantation versus Cell Homing", Tissue Engineering Part B: Reviews, 16(2): 257-262 (2010).

Pereira, et al., "Long-term fate of transplanted autologous fat in the face", Journal of Plastic, Reconstructive & Aesthetic Surgery, 63(1):e68-69 (2010).

Shandalov, et al., "An engineered muscle flap for reconstruction of large soft issue defects," Proceeding of the National Academy of Sciences of the United States of America, 111(16): 6010-6015 (2014).

Sterodimas, et al., "Tissue engineering with adipose-derived stem cells (ADSCs): Current and future applications", Journal of Plastic, Reconstructive & Aesthetic Surgery, 63:1886-1892 (2010).

Wei, et al., Chapter 5—"Polymeric Biomaterials", Handbook of Biopolymers and Biodegradable Plastics, 87-107 (2013).

Cascone, et al., "Hydrogel-based commercial products for biomedical applications: A review", International Journal of Pharmaceutics, 118803 (2019).

European Search Report for EP application 19717107.7-1109 dated Dec. 9, 2022.

* cited by examiner

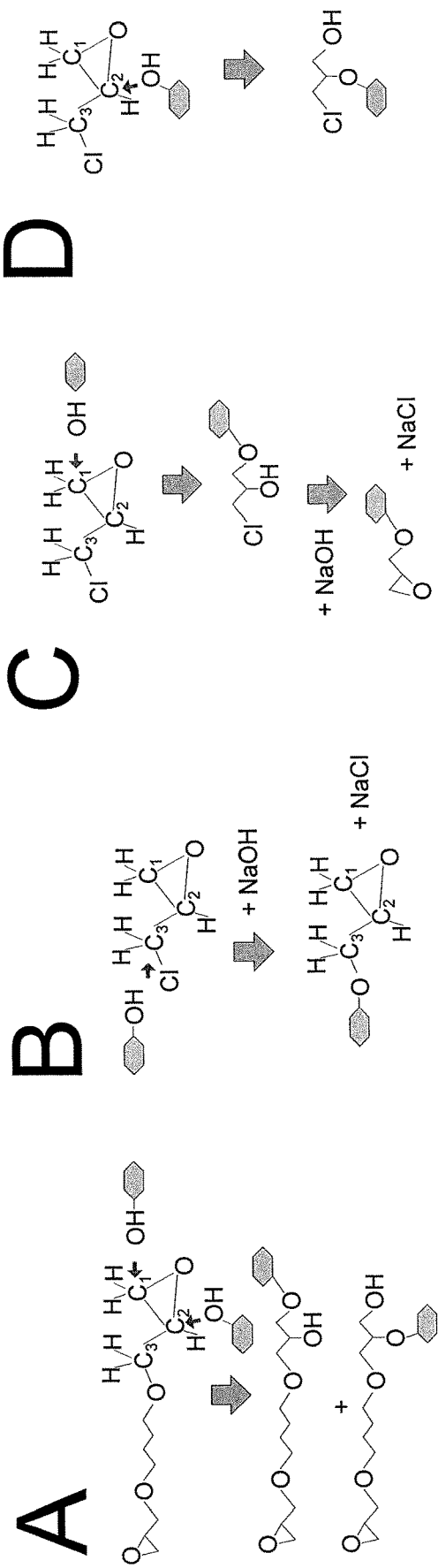
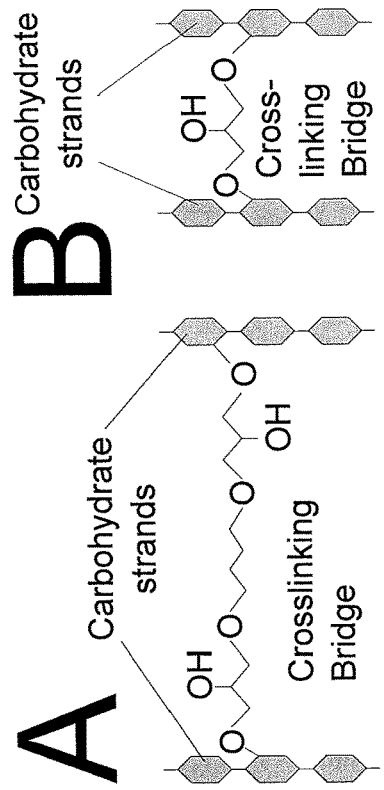
Fig. 1
Fig. 2

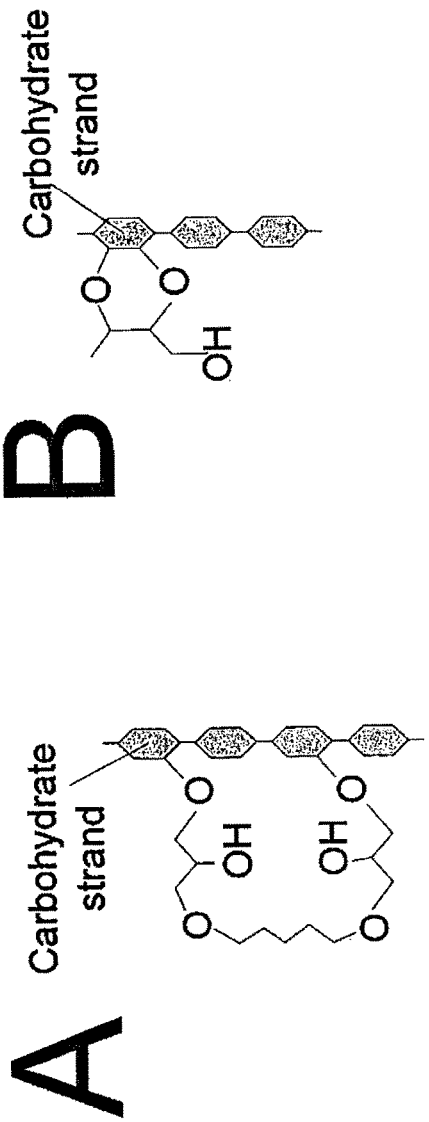
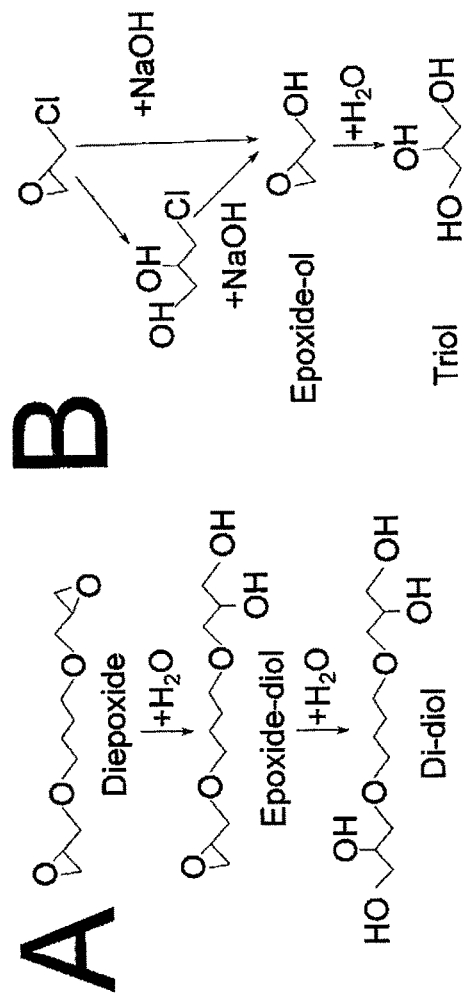
Fig. 5
Fig. 6

HE stainings of implant area, 3 months after the implantation or injection procedure.

COMPOSITION COMPRISING A CROSS-LINKED POLYOL

CROSS-REFERENCE TO RELATED APPLICATIONS

This application is a National Phase application under 35 U.S.C. 371 of PCT/CH2019/000009, filed Apr. 2, 2019, the disclosure of which is hereby incorporated herein by reference in its entirety.

The invention relates to a composition comprising a polyol crosslinked with a multi-functional epoxide or an epihalohydrin or a molecule or crosslinker mixture comprising multiple epihalohydrin and/or epoxide groups or molecules.

The composition is useful for a variety of implants, in particular for tissue engineering materials.

Definitions

Tissue Engineering Material

A biocompatible material for use in reconstruction, repair, enhancement, augmentation or substitution of tissues or organs. In the context of this invention, a material obtained by combination of the branched-sheet 3D particles with a physiologically acceptable fluid (physiological saline, phosphate buffered saline, blood plasma, living aspirates such as lipoaspirate).

Dry Mass Concentration

The dry mass concentration of the tissue engineering material can be determined by standard techniques known in the art, i.e. washing of the particles to remove salts followed by drying to constant weight, and relating the dry weight found in this way to the volume of the soft tissue engineering material.

BRIEF SUMMARY OF THE INVENTION

The composition according to the invention may be used as a tissue or organ body implant. The implantable composition according to the invention may also be used for treating tissue defects, in particular tissue defects caused by severe trauma or cancer ablation. Further the composition may be used for aesthetic restorations in the face and the body. It may also be used for cell transplantation and drug delivery, and in-vitro purposes such as cell culture.

The invention provides a composition resulting from efficient crosslinking of carbohydrates and generally polyols with at least bifunctional epoxides or also epihalohydrins. It provides methods to overcome a general problem observed in crosslinking of carbohydrates or more generally polyols with epoxides or epihalohydrins: in addition to effective crosslinks, numerous pendant groups result. The associated incorporation of excessive amounts of crosslinker raises toxicological concerns. The invention discloses a method to substantially remove water before creating conditions allowing to initiate the crosslinking, thereby dramatically reducing the pendant groups in favor of crosslinks.

Further advantageous embodiments of the invention can be commented as follows:

The polyol purposefully is a molecule having at least two hydroxyl groups and a molecular weight of at least 0.5 kDa, preferably at least 1.0 kDa. In a special embodiment of the invention the polyol is a carbohydrate or an anionic carbohydrate. The carbohydrate can be (i) a polysaccharide, preferably a negatively charged polysaccharide;
(ii) an alginate;
(iii) hyaluronic acid; or
(iv) a carboxymethylcellulose.

These materials confer elasticity to the particle enabling a reversible compression capability and a reversible fluid intake capability.

The multi-functional epoxide purposefully is a di-epoxide, preferably ethylene glycol-diglycidyl ether or butanediol-diglycidyl ether.

In a preferred embodiment of the invention the relationship between $N_1$ and $N_2$ is: $N_1 > 0.45 (N_1+N_2)$, more preferentially $N_1 > 0.5 (N_1+N_2)$ and most preferentially $N_1 > 0.55 (N_1+N_2)$.

The relative amount of doubly crosslinked hydroxide groups in the polyol compared to the total amount of reactive hydroxyl groups before crosslinking of the polyol is purposefully comprised between 0.1% and 10% and preferably between 0.5 and 5%.

The concentration of the $N_3$ ether groups with a reactive epoxy group purposefully is below 50000 micromoles/kg of dry mass of the composition and preferably below 5000 micromoles/kg of dry mass of the composition. The concentration of the $N_3$ ether groups with a reactive epoxy group is preferably below 500 micromoles/kg of dry mass of the composition and most preferably below 50 micromoles/kg of dry mass of the composition. The concentration of the $N_3$ ether groups with a reactive epoxy group may be below 5 micromoles/kg of dry mass of the composition and preferably below 1 micromoles/kg of dry mass of the composition. A composition with these concentrations of the $N_3$ ether groups has the advantage that it exhibits a low residual toxicity and therefore is useful for a direct implantation into the body of a patient for purposes of tissue engineering, or drug release.

Purposefully the concentration of the $N_3$ ether groups with a reactive epoxy group is above 50 micromoles/kg of dry mass of the composition. Such a composition is suitable to be used for attaching proteins, antibodies, catalysts or enzymes.

The centration of soluble free di-epoxide species in the composition purposefully is lower than 100 nanomoles/g of dry weight of the composition, preferably lower than 25 nanomoles/g of dry weight of the composition and most preferably lower than 2.5 nanomoles/g of dry weight of the composition.

The concentration of soluble free mono-epoxide species in the composition is purposefully lower than 2000 nanomoles/g of dry weight of the composition, preferably lower than 1000 nanomoles/g of dry weight of the composition.

The concentration of soluble free mono-epoxide species in the composition is purposefully lower than 250 nanomoles/g of dry weight of the composition, preferably lower than 25 nanomoles/g of dry weight of the composition. The amounts of free floating residues of the di-epoxide (either free di-epoxide or free mono-epoxide) are critical since they will cross-link DNA which may create mutations.

In a special embodiment the composition has a fractured structure comprising a multitude of individual particles, preferably with a size of less than 5 mm, most preferably of less than 2 mm. In this form the composition can be used as an implant material, cell-culture carrier, wound healing material, surgical mesh or contact lenses. Preferably the particles have a number of protrusions at their surfaces. Preferably the particles are internally built in the manner of spicula.

In further embodiment of the invention the composition comprises a multitude of interconnected pores.

In the elemental analysis of the dry mass of the composition the atomic number of all elements occurring at more than 10 mol % is preferably 12 or below.

The composition may be in a non-hydrated state. In this un-hydrated state the composition has a better long-term storage than in the hydrated state. The dry state is useful for applications where molecules will be grafted to the reactive epoxy groups which otherwise have more chances to be hydrolyzed (if stored in a hydrated state), such as the fabrication of micro-objects used for cell culture, drug/antibody delivery, and chromatography.

Alternatively the composition may be in a hydrated or partially hydrated state. In a hydrated state the composition is useful for cell culture, cell delivery, tissue engineering, as bulking agent, drug delivery, antibody delivery, in vivo cell culture, 3D in vitro models for cell culture, tissue stabilization, voids filling and for tissue augmentation (e.g. soft tissues, brain or incontinence management.

The ratio $A_W:A_D$ between the volume $A_D$ of dry mass and of the volume $A_W$ of water in the composition is purposefully 1.7 to 2.3, preferably 1.9 to 2.1.

In another embodiment the composition further comprises a physiologically acceptable fluid for implantation of the composition into a human or animal. The fluid may be water, an aqueous solution, blood or adipose tissue. The physiologically acceptable fluid has purposefully a viscosity in the range of 0.5 mPa·s and 300 mPa·s, and preferably in the range of 1 mPa·s and 50 mPa·s. The flowability of the suspension of the particles is considerably improved by suspending the particles in a viscous fluid, such as a solution of monomers or a polymer solution.

The composition may be in the form of a malleable paste.

The amount of dry mass in 1000 cm$^3$ of the hydrated composition is purposefully comprised between 2 g and 100 g, preferably between 5 g and 50 g and most preferably between 10 g and 20 g.

The total concentration of leachable molecules with epoxide or halogen functionalities is purposefully below 200 ppb, preferentially below 20 ppb, and even more preferentially below 2 ppb.

A possible method for producing the composition according to the invention comprises the following steps:
A) Dissolving a polyol and a multifunctional epoxide in a solvent to form a solution;
B) Cooling the solution to a temperature below the crystallization point of the solvent to form an at least partially frozen solution;
C) Lyophilizing the at least partially frozen solution; and
D) Heating the lyophilized product obtained in step C) in order to cross-link the polyol.

The important advantage of this method according to the invention is to be seen in the fact that by freezing the solution in, step B) the possible cross-linking reaction is inhibited; the subsequent lyophilization of the at least partially frozen solution leads to the removal of the solvent (e.g. water). Only then the frozen solution is heated so that cross-linking can take place but without the presence of the solvent (e.g. water).

The polyol used in this method is purposefully a molecule having at least two hydroxyl groups and a molecular weight of at least 0.5 kDa, preferably at least 1.0 kDa. The polyol may be a carbohydrate or an anionic carbohydrate. The multi-functional epoxide is purposefully a di-epoxide, preferably ethylene glycol-diglycidyl ether or butanediol-diglycidyl ether.

A further method for producing the composition according to the invention comprises the following steps:

A) Dissolving a polyol and a epihalohydrin crosslinker, preferably a multifunctional epihalohydrin crosslinker with halogen and/or epoxide groups in a solvent to form a solution;
B) Cooling the solution to a temperature below the crystallization point of the solvent to form an at least partially frozen solution;
C) Lyophilizing the at least partially frozen solution; and
D) Heating the lyophilized product obtained in step C) in order to cross-link the polyol.

Purposefully after the lyophilization of step C) in the methods according to the invention at least 50%, more preferentially 80%, even more preferentially 90% and most preferentially more than 95% of the originally present epoxide groups remain present in the product obtained.

During the heating of step D) purposefully at least 50%, more preferentially 80%, even more preferentially 90% and most preferentially more than 95% of the epoxide groups present after step C) are reacting.

The composition obtained after step D) of the methods according to the invention may be optionally fragmented in either dry or hydrated state, before being purified by repeated washing cycles induced by addition of washing solution followed by removal of washing solution by application of a suitable pressure differential to the composition placed on a mesh or filter membrane, with optional incubation steps with chemical inactivation solutions or adsorption agents, optionally at elevated temperatures.

The cooling in step B) of the methods according to the invention is preferably performed at least 6° C. below the crystallization point of the solvent.

The solvent to be used in the methods according to the invention can be chosen from the group of: water, acetone, mix of water and acetone; lower alcohols, preferably isopropanol, methanol, butanol or ethanol; DMSO, dichloromethane, ionic liquids.

The temperature in step D) of the methods according to the invention is purposefully in the range of 20° C. to 150° C., preferably in the range of 40° C. to 100° C., and most preferably in the range of 50° C. to 80° C.

The duration of step D) of the methods according to the invention is purposefully in the range of 10 s to 1 week, preferably in the range of 1 min to 48 h. The duration of step D) may be in the range of 10 min to 24 h and preferably in the range of 20 min to 2 h.

In a further embodiment of the method according to the invention a catalyst for the cross-linking reaction is added
 a) either to the solution in step A); or
 b) during/after the lyophilisation in step C), preferably by spraying.

The catalyst may be chosen from the group of: Lewis acids, Bronsted acids and bases, wherein said Lewis acids and Bronsted acids and bases are water stable. Examples of catalysts are the following: Phosphoric acid, aluminium chloride, Ti(iOpr)4, amberlyst resin, montmorillonit, epoxide hydrolase, soluble epoxide hydrolase, and mixtures thereof.

The pH value as measured before step B) is preferably maintained constant by adding a base during steps C) and D).

The freezing in step B) is preferably performed homogenously throughout the solution.

Preferably interconnected pores are produced during freezing of step B).

After step D) a further optional step E1) may be performed comprising the washing of the product obtained in step D) with water.

After step D) a further optional step E2) may be is performed comprising the washing of the product obtained in step D) with a nucleophilic agent.

After step D) a further optional step E3) may be performed comprising the washing of the product obtained in step D) with an absorbing agent.

In a special embodiment of the invention the polyol has a molecular weight of 50 Da-10 MDa; preferably of 1 kDa to 1 MDa, and most preferably of 10 kDa to 500 kDa.

In a further embodiment of the method according to the invention the composition obtained after step D) is partially or fully hydrated in a further method step. The hydrated state may be obtained by adding an aqueous solution (e.g. injectable saline buffer, water or PBS) to the dry scaffold material. This can be done simply by pouring the aqueous solution on the scaffold material. A fully hydrated state is obtained when the volume of aqueous solution added is equal or superior to the volume of the scaffold "cake". A partial hydration level is obtained by adding a volume of aqueous solution inferior to the volume of the "scaffold" cake. The volume of scaffold cake can be obtained by measuring the three dimensions of the scaffold cake.

Example: In order to hydrate the composition according to the invention, the scaffold composed of the composition of the invention is placed in a clean container. A volume equivalent to the volume of the scaffold produced of injectable saline solution is added to the scaffold material.

The scaffold material is fully hydrated. The fractioning can be performed either on the dry scaffold cake or on a hydrated scaffold cake. Example: a dry scaffold of the composition of the invention is placed into a clean pouch mag and mashed mechanically until obtaining several small pieces of material.

In a further embodiment a volume of aqueous solution equal to 45% to 55%, preferably of 48% to 52% of the volume of the polyol obtained by one of the methods according to the invention is added to the latter.

The composition obtained after step D) may be is fractioned in a further method step. The fractioning can be performed either on the dry scaffold cake or on a hydrated scaffold cake. Example: a dry scaffold of the composition of the invention is placed into a clean pouch mag and mashed mechanically until obtaining several small pieces of material.

The composition according to the invention may be used an implantable tissue engineering material, preferably a soft tissue engineering material. The composition is also useful as a shapeable tissue or organ body implant.

The composition according to the invention may be used in a method for treating tissue defects, in particular tissue defects caused by severe trauma or cancer ablation. It can be further used in a method of breast reconstruction or lipofilling. It is also useful for aesthetic restorations in the face and the body.

The composition can also be used in a method of brain surgery, in particular for filling cavities left by defect, stroke, accident or malformation and for creating a new volume.

The composition is useful in particular in a method of:
Cell delivery into body tissues or, body organs or, body fluids;
Cell culture, differentiation, preparation, with or without subsequent in-vivo delivery
In vivo cell culture for the production or consumption of differentiating factors, antibodies, hormones, cells, genetic vectors, vessels, red blood cells, white blood cells, stem cells, exosomes, lipids, energy, heat or, light;
Lifting or expanding tissues, in particular skin tissues, breast tissues or supporting sphincters;
Preventing tissue adhesions;
Enhancement of soft tissues volumes;
Create synthetic cellular organizations, in particular in the ovarian environment;
Provide patches of tissues or material for cardiac tissue repair; or
Drug delivery, coating, retaining, delivering molecules (drugs, proteins, nucleic acids, viruses, differentiation factors, growth factors, carbohydrate, adjuvants, fatty acids, triglycerides, cholesterol, with loading before, during or after delivery).

A BRIEF DESCRIPTION OF THE DRAWINGS

The invention is further directed to a method for producing the composition according to the invention which will be described in more detail below by way of example and with reference to the accompanying drawings in which:

FIG. 1 represents the chemical reaction of a carbohydrate moiety with a bifunctional epoxide (A), or an epihalohydrin (B,C,D);

FIG. 2 represents the chemical reaction between pendant epoxide groups obtained in the reaction according to FIG. 1 with another carbohydrate residue;

FIG. 5 shows the intramolecular crosslinking;

FIG. 6 shows the structure of major small molecular products obtained;

Figure 19:
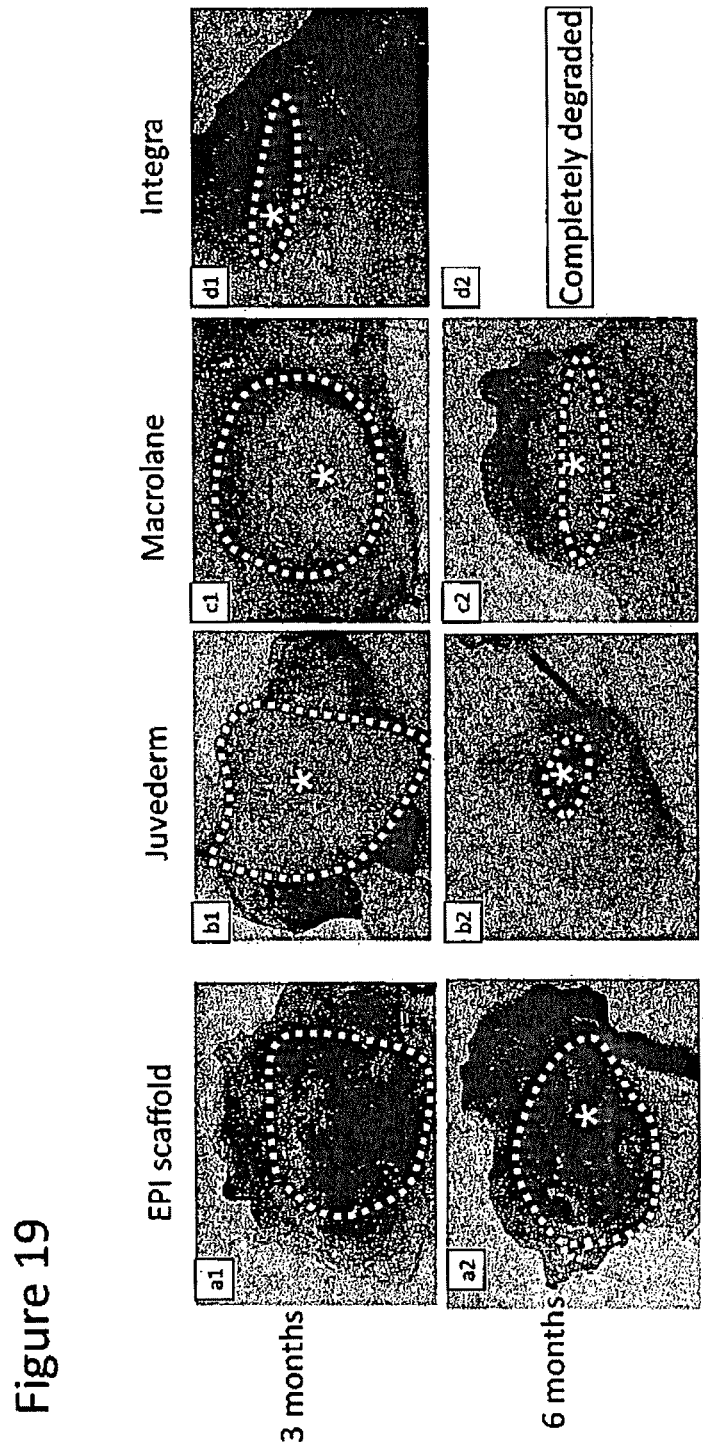
Figure 20:
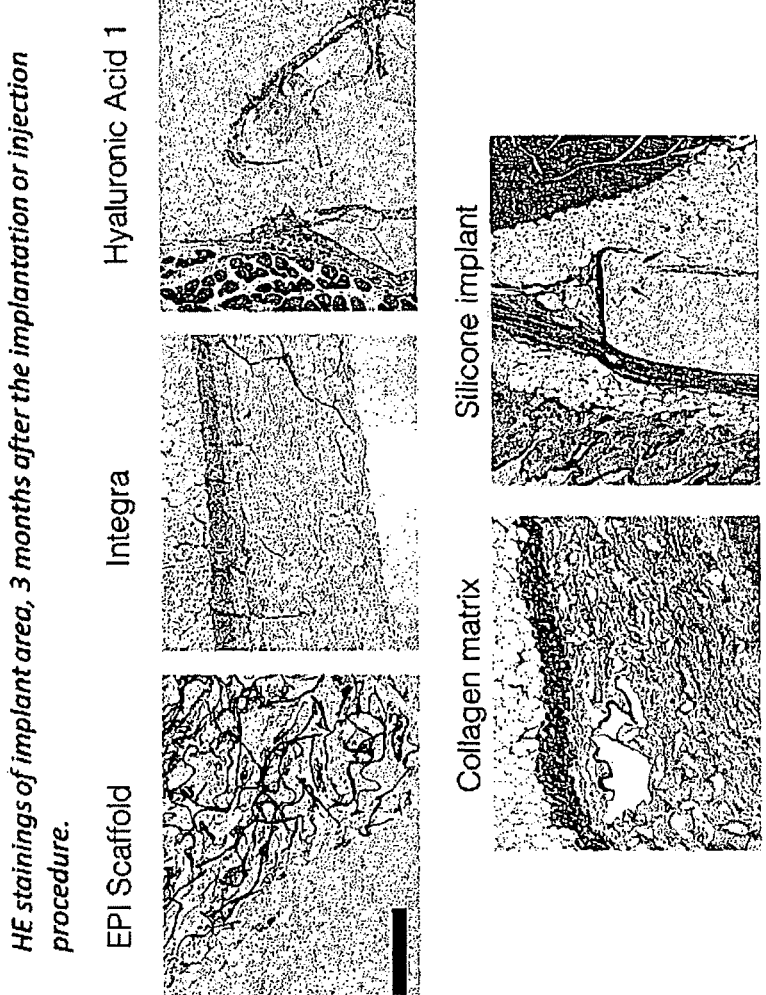

FIG. 1.8 shows representative macroscopic pictures of mice injected with the different tested materials;

FIG. 19 represents macroscopic pictures of explanted samples of different materials; and FIG. 20 shows representative H&E pictures of the different tested items.

FAVORED CHEMICAL REACTION

The basic reaction of the method according to the invention is favoring the ring-opening of bifunctional (multifunctional more generally) epoxides or epihalohydrins to crosslink carbohydrates (polyols more generally). For successful crosslinking, at least a bifunctional epoxide is necessary; an epihalohydrin by itself is sufficient for crosslinking, as both the epoxide and the halogen substituent are electrophilic sites permitting reaction with the polyol.

As a first step, an epoxide or epihalohydrin group reacts with a carbohydrate (polyol) residue as shown in FIG. 1. For a bi- or multifunctional epoxide this leads to the formation of pendant epoxide group(s). For an epihalohydrin, the major product under basic conditions is also a pendant epoxide, but halogen-substituted alcohols (FIG. 1D) are also possible as a more minor species. In any case, these intermediate present remaining electrophilic sites for further reaction.

FIG. 1 shows the reaction of a carbohydrate moiety via a hydroxyl group with a bifunctional epoxide (A; in the example, butanediol-diglycidyl ether) or an epihalohydrin (B,C,D); in the example, epichlorohydrin). A) Regio-isomers on both the carbohydrate (depending on the reacting hydroxyl group) and the epoxide (depending on the attack on $C_1$ or $C_2$; there is only attack on either $C_1$ or $C_2$ as ring opening leads to epoxide deactivation) will be formed. The reaction leads to the formation of a pendant, active epoxide group. The example is given with butanediol-diglycidyl ether as the bifunctional epoxide, but any other diepoxide or multifunctional epoxide will act in the same way. B,C,D) Epihalohydrins present three electrophilic sites: the carbon atoms of the epoxide ring, but also the carbon atom bound to the halogen substituent. B) They can react by Williamson-type nucleophilic substitution on the carbon atom bound to the halogen substituent (here $C_3$), leading to a pendant epoxide moiety. C) Attack on the epoxide is also possible, and more likely on the less substituted carbon atom ($C_1$). This results in the formation of an intermediate halohydrin (halogen substituent next to a hydroxyl group). Under consumption of base, formation of the epoxide takes place by cyclization such that again a pendant epoxide is obtained. D) Attack on the $C_2$ atom of the epoxide group results in a 3-chloro-1-ol derivative. Due to steric hindrance, pathway C) with formation of a pendant epoxide is generally expected to be favored over 0). Multifunctional epoxide or epihalohydrins will also react similarly for a given epoxy (or halogen) group, but there will be more than one remaining pendant group (halogens and epoxides possibly in various combinations or alone).

The next step is the chemical reaction of the remaining, pendant epoxide group (or possibly the halogen moiety) with another carbohydrate residue is represented in FIG. 2.

By a second ring opening reaction from the pendant epoxide groups (FIG. 1A) a crosslinking bridge is formed. A) The example is given with butanediol-diglycidyl ether as the diepoxide, but any other diepoxide will react in the same way. B) Crosslinking bridge resulting from the complete reaction of an epihalohydrin (here, epichlorohydrin). Since the nucleophilic substitution of the halogen group does not create a hydroxyl group, the crosslinking bridge will have a hydroxide group less for every halogen group. In the case of multifunctional epoxides or epihalohydrins, there will be additional pendant groups even after the completion of a crosslinking bridge, with the possibility to create multiple levels of crosslinking admixed with multiple pendant groups.

Competing Reactions

The main competing side reaction in the presence of water is epoxide or halogen group hydrolysis. Depending on when this occurs, different by-products can be formed.

Intramolecular nucleophilic reactions are intermediate between side reactions and effective crosslinking. If they occur at longer distances, one would expect them to interact synergistically with true crosslinks to contribute to hold the polymer chains together; if they occur on short distances and particularly between neighboring hydroxyl groups in the polyol, they form ineffective pendant groups.

Pendant Hydrolyzed Group

Figure 3:
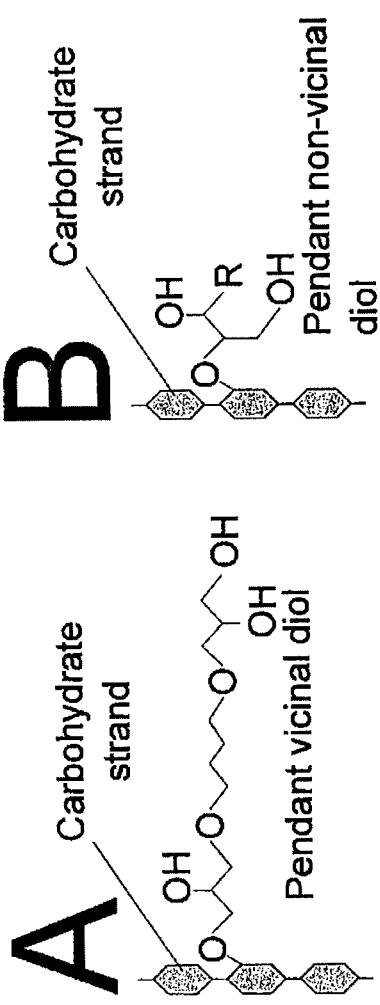
FIG. 3 shows the chemical structure of pendant inactivated groups.

If one of the epoxides of the bifunctional epoxide undergoes the desired reaction with the carbohydrate, but the other gets hydrolysed, a pendant vicinal diol/single hydroxyl group results, but no effective crosslink is formed as shown in FIG. 3.

FIG. 3A shows the pendant inactivated groups. A) The pendant vicinal diol groups arise from effective ring-opening crosslinking of one epoxide group and hydrolysis of the other. As before, the example is with butanediol-diglycidyl ether, but similar pendant groups would result for any other bifunctional epoxide.

FIG. 3B shows the reaction for an epihalohydrin (here, with a substituent R that could contain further reactive halogen or epoxide groups). Hydrolysis can also give rise to non-vicinal diols (from attack on the inner carbon atom, see FIG. 1D, followed by hydrolysis of the resulting halogenated compound). The example is given with 5-chloropentane-1,2-epoxide, but would be similar with any other halogenated epoxide (haloepihydrin). For multifunctional epoxides, there can be mixture of remaining epoxides and diols in addition to the case with remaining pendant diols only; for halogenated compounds, halogen moieties can remain as well as the mono-hydroxide groups resulting from their hydrolysis.

Pendant Electrophilic Groups

Figure 4:
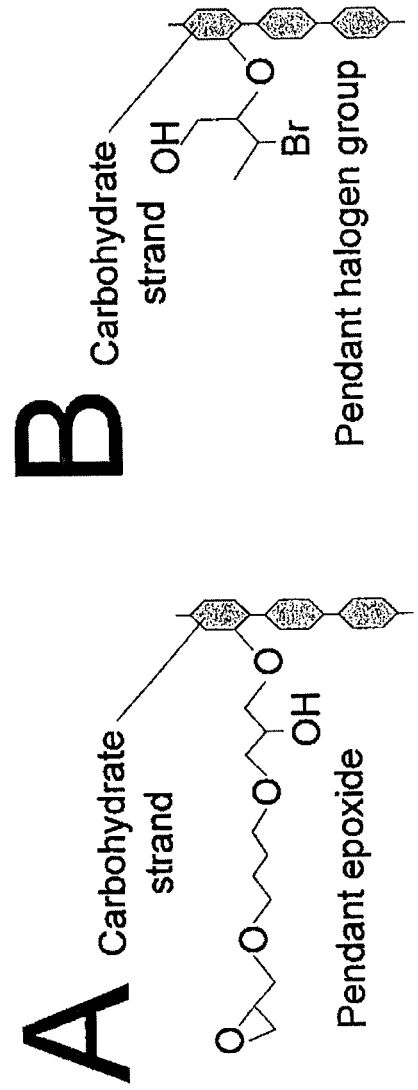
FIG. 4 shows the chemical structure of pendant electrophilic groups.

The pendant reactive groups are shown in FIG. 4.

As represented in FIG. 4A a pendant epoxide resulting from the reaction with butanediol-diglycidyl ether; any other diepoxide, will however lead to similar pendant groups.

In FIG. 4B a pendant halogen group is shown, resulting from epoxide ring opening in 3-Bromo-butane-1,2-epoxid. Conservation of the halogen moiety in another halogen-substituted epoxide will result in a similar pendant halogen group. In the case of multifunctional epoxides (or epihalohydrins), there can mixtures of pendant diols and pendant epoxide groups (and halogen moieties if part of the crosslinker).

A pendant epoxide group results from a diepoxide which reacts on one side with the carbohydrate strands, but remains unmodified on the other side. A pendant halogen group results from the reaction of a mixed halogenated/epoxidized compound while conserving the halogen group from hydrolysis. Pendant epoxides or halogen groups are an intermediate in the synthesis of the crosslinking bridges (FIG. 1, FIG. 2), but they also remain in the final product if the reaction is stopped before going to completion.

Intramolecular Reaction

The intramolecular crosslinking is explained in FIG. 5.

FIG. 5A shows an intra-molecular crosslinking by a bifunctional epoxide (here, butane-diol-diglycidyl ether). Due to the length of the diepoxide, the intramolecular crosslinking does not necessarily concern close hydroxyl groups and depending on the arrangement of true intermolecular crosslinks, the intramolecular crosslinks contribute to various extents to efficient crosslinking of the gels.

FIG. 5B shows the reaction for epihalohydrins. The molecular arrangement is such that nucleophilic substitution on neighboring hydroxyl groups is typically favored, leading to frequent 1,4-dioxane structures.

Small Molecule Hydrolysis Products

Hydrolysis of one or both of the epoxide groups (or synonymously, halogen groups) without reaction with the carbohydrate can also occur, leading to mono- and dihydrolyzed bi-products as shown in FIG. 6.

The major small molecule products are shown in FIG. 6. Various stereo-isomers exist: Diepoxide as shown in FIG. 6A. The example is given with butanedioldiglycidyl ether.

Two stages of hydrolysis occur: First, the diepoxide is hydrolyzed to an epoxide-dial, and then to a di-diol with two vicinal diol groups.

FIG. 6B refers to the hydrolysis of an epihalohydrin (here, epichlorohydrin) which also occurs in two stages. In the first stage, either the halogen substituent or the epoxide groups are hydrolysed. This results either directly (for hydrolysis of the halogen substituent) or indirectly by intramolecular epoxidation under base catalysis (for primary hydrolysis of the epoxide) in a epoxide-ol (glycidol or a derivative thereof, depending on the original epihalohydrin). In a second stage, the epoxide-ol (glycidol derivative) is hydrolysed to a trial (glycerol or one of its derivatives). For multifunctional or mixed halogenated/epoxided compounds, various combinations of vicinal diols, isolated hydroxyl, halogen groups.

Concentration of the Reaction Products

Main Fates of an Epoxide Group

Figure 7:
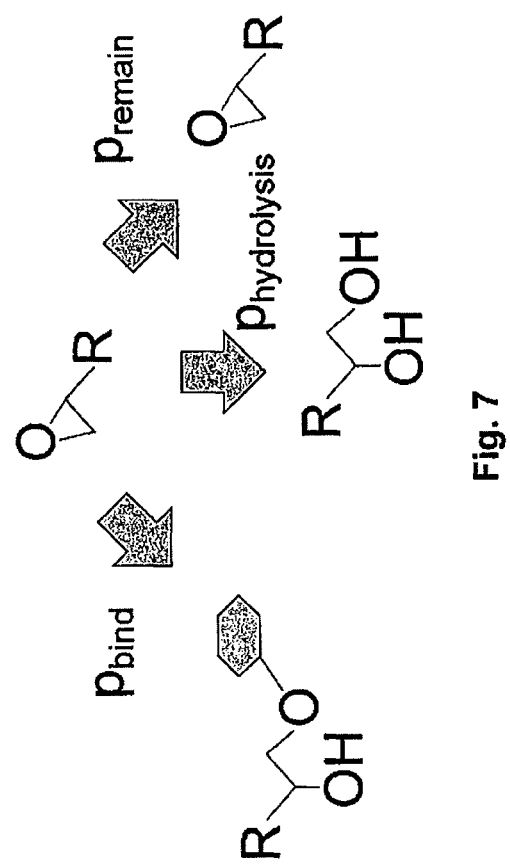
FIG. 7 shows the main fates of an epoxide group.

The main fates of a given epoxide group are represented in FIG. 7. Binding, hydrolysis or remaining intact are the main possibilities for an epoxide, whether we consider diepoxides, epihalohydrins, or multifunctional epoxides/epihalohydrin species. The aim of this invention is to maximize the probability of covalent binding to the polyol ($p_{bind}$). Minor side reaction can also occur (ester bond formation in the presence of carboxylates, self-polymerization of the crosslinker) but are not shown here.

Given its possibility to reform an epoxide group upon reaction with a carbohydrate, an epihalohydrin group behaves functionally like a diepoxide. Upon binding to the polyol ($p_{bind}$), the typical result is a pendant epoxide group, rarely a pendant halogen group. Likewise, hydrolysis (with probability $p_{hydrolysis}$) typically leads to a hydroxylated derivate (a glycidol derivative).

Main Fates for Crosslinker Molecules

The fates of the crosslinker molecules are related to the fates of their functional groups. However, since there are several (at least 2) reactive sites on each crosslinker molecule, the probabilities for the fates of the crosslinkers is are non-trivially related to the underlying probabilities for the functional groups shown in FIG. 7, and it is generally necessary to distinguish between fate probabilities for entire crosslinker molecules and the fate probabilities for the individual reactive groups.

Incorporation

Figure 8:
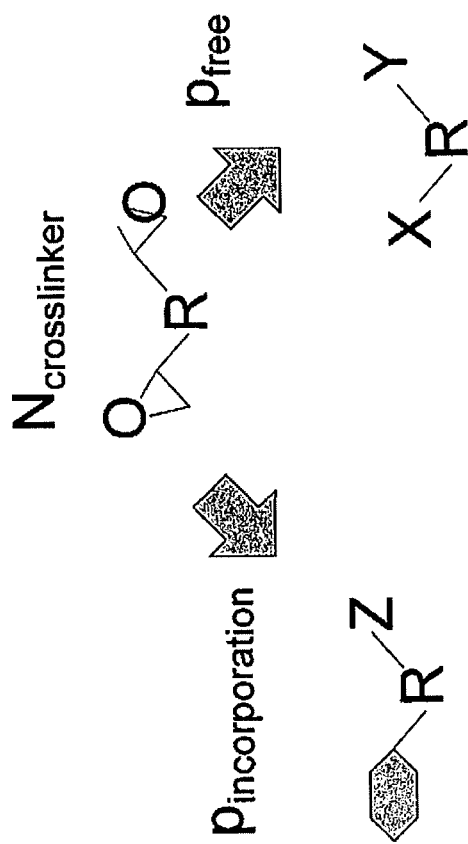
FIG. 8 represents the fate decisions for a di-epoxide molecule.

FIG. 8 illustrates the fate decision for a crosslinker molecule (here, a generic diepoxide). If at least one of its reactive groups reacts with the carbohydrate (or polyol in general), it becomes incorporated into the final polymer; the other group still has various possibilities (remaining, hydrolysis, crosslinking or some side reaction), and is therefore labeled Z. If none of the two epoxide groups reacts with the carbohydrate (polyol), the diepoxide remains as a free small molecule, its epoxide groups having various reaction possibilities symbolized by X and Y. With few changes, epihalohydrins functionally behave like diepoxides: Incorporation typically leads to a pendant epoxide group (FIG. 1B, 1C), more rarely to a pendant halogen group (FIG. 10), which nevertheless retains reactivity for a subsequent nucleophilic reaction, and so shows the same basic functionality as a diepoxide. If an epihalohydrin remains unbound, various combinations X,Y of intact, partially or fully hydrolysed molecules are possible as for the diepoxides. For multifunctional epoxides/halogen compounds, incorporation necessitates the reaction of at least 1 out of the n reactive groups with the carbohydrate.

In the general case, the successful reaction of at least one out of n reactive epoxide (or halogen) groups is sufficient to lead to incorporation of the crosslinker into the final polymer molecule.

Crosslinking

Figure 9:
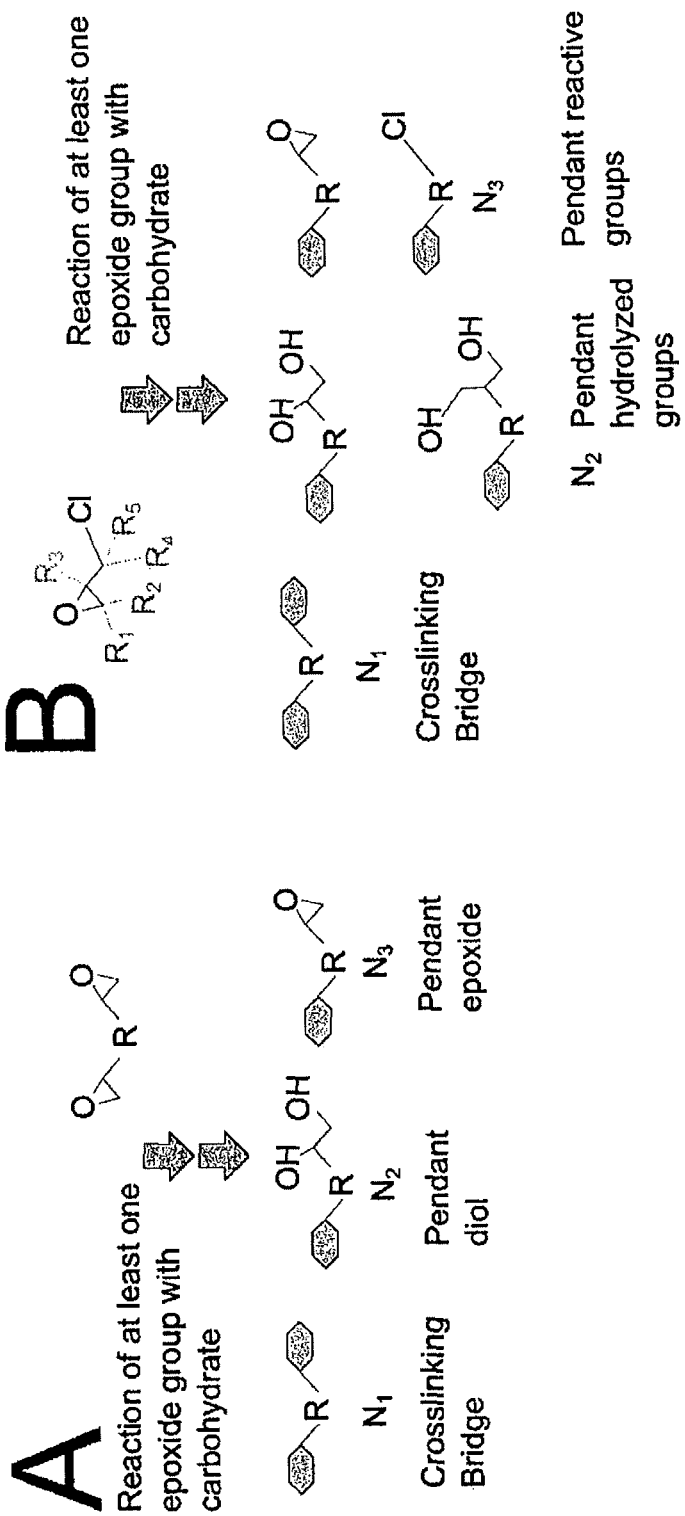
FIG. 9 shows some incorporated bound moieties.

For all incorporated crosslinker molecules, at least one reactive group (epoxide or halogen group) has reacted with the polyol (in a minority indirectly via grafting onto a newly created hydroxyl group from an epoxide opening reaction with the carbohydrate backbone). The other group(s) of the crosslinker may react with the polyol as well (leading to a crosslinking bridge, FIG. 2), get hydrolysed (leading to a pendant vicinal diol, FIG. 3) or remain as epoxide (FIG. 4). These possibilities are succinctly represented in FIG. 9 which shows the bound moieties.

FIG. 9A shows the reactions for a diepoxide. If both of the epoxide groups of the diepoxide react with the carbohydrate, a crosslinking bridge is formed (see FIG. 2); if one epoxide group reacts with the carbohydrate (see FIG. 8), but the second becomes hydrolysed, a pendant vicinal diol is formed (see FIG. 3); finally, if one epoxide reacts with the carbohydrate but the other remains unchanged, a pendant epoxide group results.

Figures 10A, 10B:
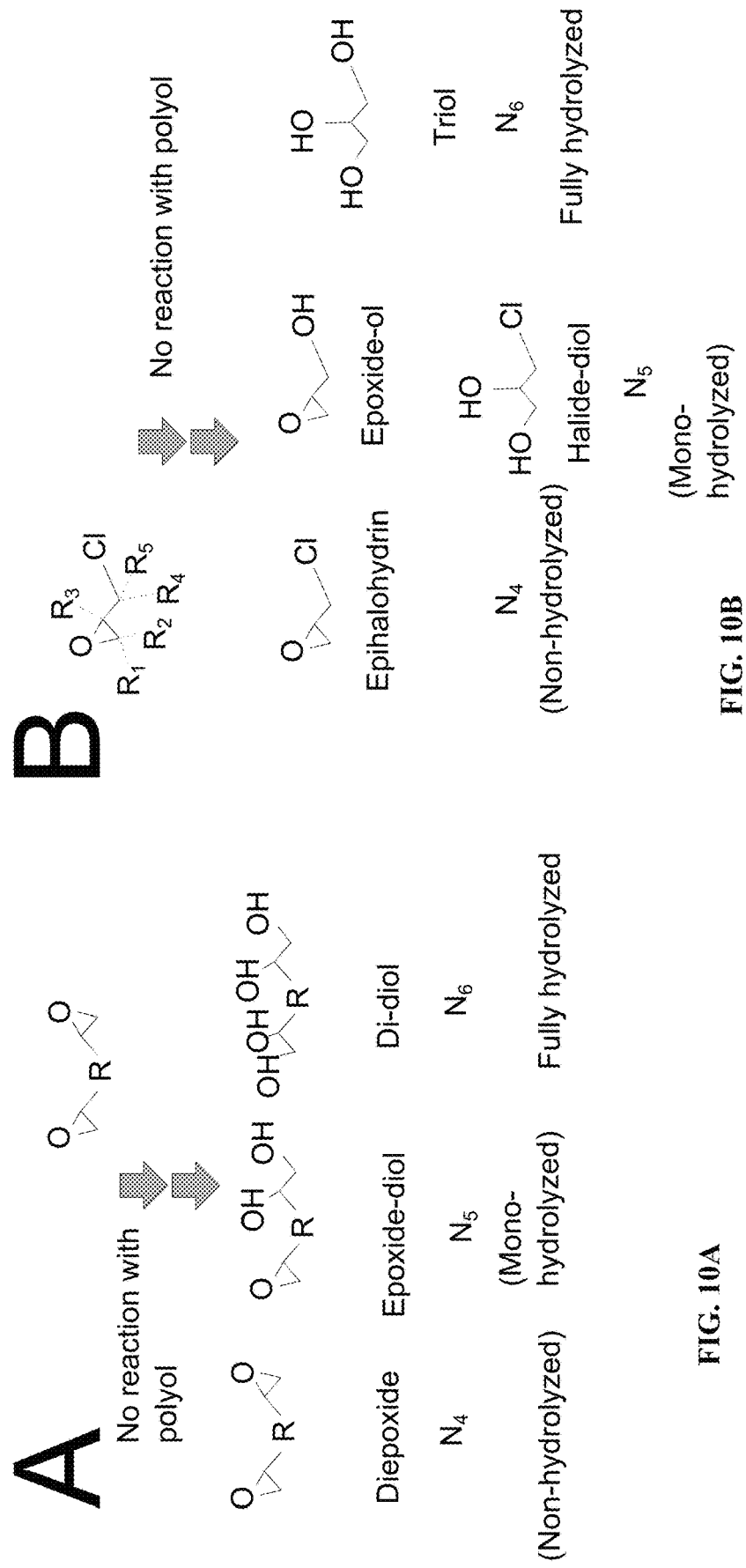
FIG. 10 shows free reactions products.

FIG. 9B shows the reactions for epihalohydrin (here, epichlorohydrin with general substitution possibilities $R_1$-$R_5$). Two successful reactions with different carbohydrate (polyol) repeat units lead to a crosslinking bridge, whereas one carbohydrate reaction combined with one hydrolysis step leads to vicinal and non-vicinal pendant diols as pendant hydrolyzed groups. A single successful reaction with the carbohydrate generates a pendant epoxide in most cases (FIGS. 1B and 1C), but possibly also a pendant halogen group (FIG. 10). Both pendant epoxide and pendant halogen conserve reactivity towards the polyol or other nucleophiles. With multifunctional epoxides or epihalohydrins, multiple combinations are possible.

To quantify the crosslinking efficiency in multifunctional epoxides and epihalohydrins, with a total of n reactive sites per molecule, detailed accounting on the fate of the individual reactive groups is needed.

Crosslinking efficiency can be estimated from the average amount of distinct carbohydrate (polyol) repeat units bound to a crosslinker molecule via ether bonds. In practice, this can for example be done by treatment of the final purified polymer under conditions that lead to complete chemical degradation of the carbohydrate (polyol) strands to their constituent repeat units, but leave intact the covalent ether bonds between crosslinkers and polyol units. Chromatographic and structural analysis of the fragments then allows to estimate the number $N_1$ of effective crosslinks contracted on average per crosslinker molecule.

This number of effective crosslinks $N_1$ per crosslinker molecule is the average number of distinct carbohydrate (polyol) repeat units bound per crosslinker molecule ($n_1$) minus 1, since binding a single carbohydrate (polyol) unit only leads to a pendant crosslinker, not an actual crosslink:

$$N_1 = \text{<Average number of effective crosslinks per crosslinker>} = n_1 - 1 \qquad \text{eq. 2}$$

Particular attention needs to be paid to the definition of $n_1$: This is not merely the number of ether bounds formed per crosslinker molecule, but $n_1$ is the actual number of distinct carbohydrate (polyol) repeat units bound directly to a crosslinker molecule via an ether bond. The distinction is important for two main reasons. First a single crosslinker molecule may form several ether bonds with the same carbohydrate (polyol) repeat unit, so that the number of ether bonds to the carbohydrate (polyol) is higher than the number of repeat units bound. Second, there can also be self-polymerization of the crosslinker molecules. This generates ether bonds, without necessarily creating crosslinks.

The average number of pendant groups $N_2$ in turn is given by the valency n of the crosslinker minus the number of bound distinct carbohydrate repeat units:

$N_2$=<Average number of pendant groups per crosslinker>=$n-n_1$=$n-1-N_1$   eq. 3

The designation of $N_2$ "pendant" groups should be understood in a large definition: it encompasses all the possibilities that fail to provide efficient ether crosslinking. This includes hydrolyzed pendant groups, remaining active pendant groups ($N_3$ in FIG. 9), but also other possibilities such as alternative bond-type formation (particularly, ester bonds if there are carboxylate groups present in the polyol), or ether bonds in self-polymerization.

To illustrate the use of eq. 2 and 3, let us consider a illustrative example of a carbohydrate crosslinked with a bifunctional epoxide such as butane-diol-diglycidyl ether, characterized by n=2. Pendant crosslinker molecules bind 1 carbohydrate repeat unit, effectively crosslinking units 2 distinct carbohydrate repeat units. Therefore, $N_1$=0 and $N_2$=1 for the pendant crosslinkers, and visa-versa $N_1$=1 and $N_2$=0 for the effective crosslinks. In a composition where 40% of the crosslinkers molecules were able to establish effective crosslinks and 60% remain pendant, the average $N_1$ is 0.4, and the average $N_2$=0.6.

From the definition of $N_1$ and $N_2$, the crosslinking efficiency can be defined:

$$\sigma = \frac{<\text{Actual number of effective crosslinks per crosslinker}>}{<\text{Possible number of effective crosslinks per crosslinker}>} = \frac{\langle N_1 \rangle}{\langle N_1 \rangle + \langle N_2 \rangle}$$   eq. 4

For bivalent crosslinkers this is the "cross-linker ratio", i.e. the ratio of crosslinking to pendant crosslinker molecules (Kenne et al., Carbohydrate Polymers 91 (2013) 410-418). Eq. 4 generalizes the concept to crosslinkers of arbitrary valency n. Eq. 4 is to be applied on the purified polymer, that is after substantial removal of non-bound crosslinker remnants.

It is important to note that eq. 4 concerns averages, denoted by the < > brackets. Individual crosslinkers molecules are present in various binding configurations within the final polymer, and ($N_1$) and ($N_2$) should be evaluated as an average over the different configurations. Averaging is obviously also necessary if a mixture of different crosslinker molecules with different valency n is used.

For a given minimal desired crosslinking efficiency $\sigma_{min}$, eq. 4 can be rewritten as:

$N_1 \geq \sigma_{min} \cdot (N_1 + N_2)$   eq. 5 where it is understood that $N_1$ and $N_2$ are the properly averaged numbers of effective crosslinks respectively general pendant groups per incorporated crosslinker molecule, as described above.

Example Evaluation of the Crosslinking Efficiency Hyaluronic Acid-Based Dermal Fillers The proportion of pendant and crosslinking bifunctional epoxide has been assessed in various dermal fillers. As an example, we use the data provided in the scientific publication: Kablik, J., G. D. Monheit, L. Yu, G. Chang, and J. Gershkovich, Comparative physical properties of hyaluronic acid dermal fillers. Dermatol Surg, 2009. 35 Suppl 1: p. 302-12.

The analysis by Kablik et al. concerns the percentage of the hyaluronic acid repeat units modified by either pendant or crosslinking bifunctional epoxides (there is also data on other crosslinkers in this publication, but this is not of relevance here). The data in Kablik et al. is reported in terms of hyaluronic acid (HA) repeat units modified with pendant or crosslinking groups. The first step in evaluation of the crosslinking efficiency from the data by Kablik et al. is to calculate the average $N_1$ and $N_2$ values according to eq. 2 and eq. 3. For this, we need to take into account the different stoichiometry for the pendant and crosslinking fragments: There is 1 crosslinker per HA repeat unit for pendant groups, but 1 crosslinker for 2 HA repeat units for the crosslinking groups.

The data in Kablik et al. is reported in terms of the concentration of hyaluronic acid (HA) repeat units present in the crosslinked respectively pendant-modified fractions. As there is only half as much crosslinker per HA repeat unit in the crosslinked fragments as compared to the pendantly modified fragments, the molar fraction of effectively crosslinking crosslinker is:

$$\theta_{crosslinking} = \frac{[\% \text{ crosslinked } HA \text{ residues}]/2}{[\% \text{ crosslinked } HA \text{ residues}]/2 + [\% HA \text{ residues with pendant group}]}$$   eq. 6

With the molar fraction of crosslinking diepoxide moieties in the final polymer, we can estimate $<n_1>$ $\langle n_1 \rangle = 2 \cdot \theta_{crosslinking} + 1 \cdot (1 - \theta_{crosslinking}) = 1 + \theta_{crosslinking}$   eq. 7 and therefore, by virtue of eq. 2:

$N_1 = n_1 - 1 = \theta_{crosslinking}$   eq. 8 and from eq. 3

$N_2 = n - 1 - N_1 = 2 - 1 - \theta_{crosslinking} = 1 - \theta_{crosslinking}$   eq. 9 and finally from eq. 4:

$$\sigma = \frac{N_1}{N_1 + N_2} = \theta_{crosslinking}$$   eq. 10

Table 1 reports the analysis of the data reported by Kablik et al. in terms of eq. 6 to eq. 9

TABLE 1

Evaluation of crosslinking efficency by eq. 14 for some hyaluronic acid crosslinkers based on bifunctional epoxides. Data from Kablik, J., G.D. Monheit, L. Yu, G. Chang, and J. Gershkovich, Comparative physical properties of hyaluronic acid dermal fillers. Dermatol Surg, 2009. 35 Suppl 1: p. 302-12.

| Product | % HA repeat units crosslinked | % HA repeat units modified with pendant group | $\theta_{crosslinking}$ (eq. 6) | $N_1$ (eq. 8) | $N_2$ (eq. 9) |
| --- | --- | --- | --- | --- | --- |
| Restylane | 1.2 | 3-1.2 = 1.8 | (1.2/2)41.2/2 + 1.8) = 0.25 | 0.25 | 0.75 |
| Perlane | 1.4 | 3-1.4 = 1.6 | (1.4/2)/(1.4/2 + 1.6) = 0.30 | 0.30 | 0.70 |
| Juvederm 30 HV | 2 | 10-2 = 8 | (212)/(2/2 + 8) = 0.11 | 0.11 | 0.89 |

We can finally state that for the diepoxide-crosslinked products analyzed by Kablik et al., we have:

Restylane:

$$N_1 = 0.25 * (N_1 + N_2) \qquad \text{eq. 11}$$

Perlane:

$$N_1 = 0.30 * (N_1 + N_2) \qquad \text{eq. 12}$$

Juvederm 30HV:

$$N_1 = 0.11 * (N_1 + N_2) \qquad \text{eq. 13}$$

Even for the Perlane and Restylane product, which are produced by efficient the Nasha™ technology, which uses transient steric hindrance to introduce high crosslinking efficiency (WO1997004012A1), the crosslinking efficiencies as evaluated by eq. 4 remain relatively low (below 0.4 even if including possible experimental errors in the analysis by degradation and chromatography).

Sephadex G-25

A further illustrative example is the evaluation of the crosslinking efficiency according to eq. 4 in the commercial chromatography medium Sephadex G-25. This data set was gathered by Holmberg et al. (Holmberg et al., Carbohydrate Research 272 (1995) 203-2011). Sephadex G-25 is not intended by tightly crosslinked, but the analysis illustrates the approach more completely since Holmberg et al. provide detailed fragment data rather than already summarized data.

TABLE 2

Evaluation of crosslinking efficiency from the data gathered by Holmberg at al., Carbohydrate Research 272 (1995) 203-2011, as an illustrative example of how to evaluate crosslinking efficiency according eq. 4

| Fragment # | Fragment stoichiometry (G = glucane unit, C = crosslinker) | Number of effective crosslinks $(n_1-1)$ | Potential number of effective crosslinks $n_1 + n_2 - 1$ | Relative concentration (expressed originally relative to glucide, here relative to crosslinker) | Comment |
|---|---|---|---|---|---|
| A | G | N.A. | N.A. | 0*55.7 | No crosslinker in this fragment, so no contribution in terms of crosslinker fate |
| B | $G_1C_1$ | 0 | 1 | 7.15 + 3.31 + 4.48 + 2.37 + 2.67 + 2.24 = 22.22 | 1,4-dioxane structure (link to single glucide) |
| C | $G_1C_1$ | 0 | | 0.94 + 2.17 + 1.10 + 4.68 + 0.27 = 9.16 | Pendant diol |
| D (2 crosslinkers) | $G_1C_2$ | 0 | | 2*(0.3 + 0.27 + 0.27 + 0.53 + 0.67) = 4.08 | Two crosslinkers pendant from a single glucide residue |
| E | $G_1C_2$ | 0 | | 0.57*2 = 1.14 | 1,4-dioxane structure formed by self-polymerization of 2 crosslinkers attached to glucide |
| F | $G_1C_2$ | 0 | | (0.77 + 0.67)*2 = 2.88 | 2 self-polymerized crosslinkers attached to glucide via 1,4-dioxane bridge |
| G | $G_2C_1$ | 1 | | 0.5*(0.5 + 0.67) = 0.585 | 1 crosslinker between 2 glucide residues |
| H (crosslinker 1) | $G_2C_1$ in overall fragment $G_2C_2$ | 1 | | 0.5*(0.7 + 0.7) = 0.7 | 1 crosslinker between 2 glucide residues |
| H (crosslinker 1) | $G_1C_1$ in overall fragment $G_2C_2$ | 0 | | 0.5*(0.7 + 0.7) = 0.7 | Pendant 1,4-dioxane structure |
| I | $G_2C_2$ | 1/2 | | 0.43 + 0.4 = 0.83 | Bridge made from 2 crosslinkers in series (1 effective crosslink per 2 crosslinkers) |

Weighted by the relative crosslinker concentrations, we have:

$$N_1 = \overline{n_1 - 1} = \frac{0 \cdot (22.22 + 9.16 + 4.08 + 1.14 + 2.88 + 0.7) + 1 \cdot (0.585 + 0.7) + 1/2 \cdot 0.83}{22.22 + 9.16 + 4.08 + 1.14 + 2.88 + 0.7 + 0.585 + 0.7 + 0.83} = 0.04$$

eq. 14

Only pure epichlorohydrin is used in the fabrication of Sephadex G-25 (Holmberg et al., Carbohydrate Research 272 (1995) 203-2011), therefore n=2 and:

$$N_2 = n - 1 - N_1 = 0.96$$

eq. 15 and ultimately:

$$N_1 = 0.04 * (N_1 + N_2)$$

eq. 16 indicating an ultimately rather low crosslinking efficiency. This is in part due to the aqueous reaction conditions used in the fabrication of Sephadex G-25 (Holmberg et al., Carbohydrate Research 272 (1995) 203-2011), favoring hydrolysis. The close spacing of the electrophilic centers in epichlorohydrin, favoring ineffective dioxane ring formation, is also of concern, particularly in dilute aqueous suspensions where the availability of hydroxyl groups from different strands is low.

Free Small Molecules

FIG. 10 shows the free reaction products (see also FIG. 6) for the chain of reactions. For multifunctional epoxides or epihalohydrins, multiple combinations are possible.

Polymer and Desired Structural Features

Figure 11:
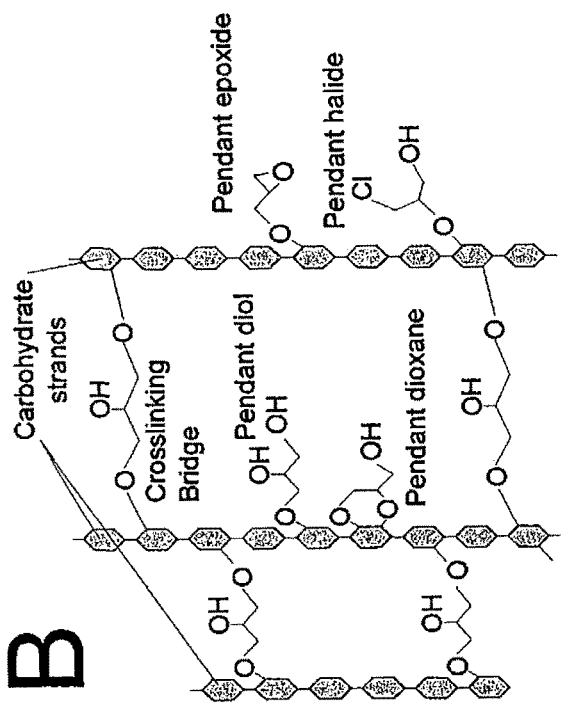
FIG. 11 is a partial view of the polymer structure.
Figure 11:
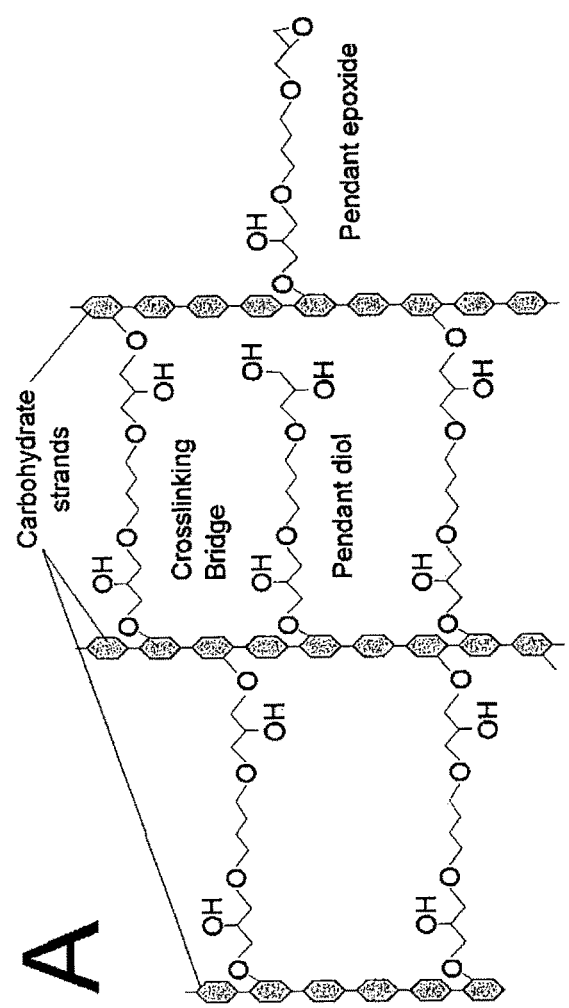
Figure 12:
FIG. 12 shows the formation of alcoholate by vigorous withdrawal of water in the presence of strong base.

FIG. 11 is a view on the polymer structure. The composition described in this invention has a low relative amounts of pendant groups (active or hydrolyzed) compared to the crosslinking bridges. In FIG. 11A the polymer structure is illustrated with crosslinks, pendant diols, and pendant epoxides resulting from the reaction with butanedioldiglycidyl ether, but similar structures would be obtained by the reaction with any other diepoxide. In FIG. 11B the polymer structure is illustrated with pendant diols, pendant epoxides, and possibly pendant halides resulting from the reaction of epichlorohydrin, but similar structures would be obtained with any epihalohydrin. For multifunctional epoxides or haloepihydrins, multiple combinations of various crosslinks and pendant groups are possible.

After purification, with near complete removal of small molecules residues, essentially only the bound structures remain. FIG. 11 gives a view on a small region of the resulting polymer network with arbitrary extension. The composition described in this invention is a material with a high relative proportion of crosslinking bridges as compared to the pendant groups. This composition is indeed minimizing the toxicity by limiting the non-carbohydrate material to a minimum, by providing only effective crosslinks and limiting the pendant groups to a minimum.

Method

The method for producing the composition according to the invention consists in a series of preparation steps, followed by an actual reaction step. The preparation steps (dissolving, freezing, lyophilizing) serve to intimately mix the reactants: carbohydrate (polyol in general), diepoxide (or multifunctional epoxide, epihalohydrins, mixed multifunction epihalohydrins end epoxides), catalyst (in the typical example, a base, but can be typically combined with further catalysts such as phase transfer catalysts) and remove water.

Figure 13:
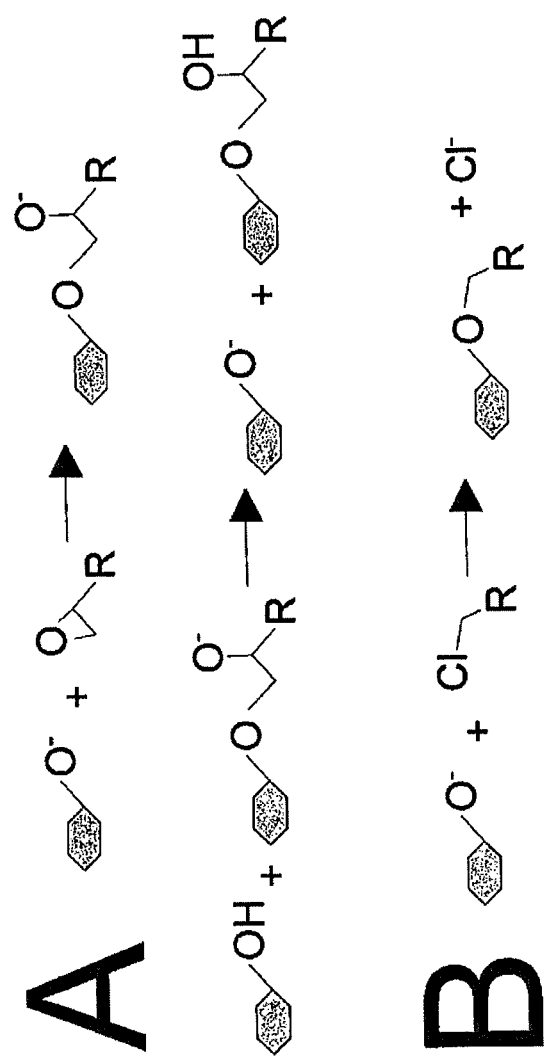
FIG. 13 shows the ring opening by anionic chain reaction.

Once most of the water is removed by lyophilization, the temperature is raised. The epoxide now readily undergoes ring opening by anionic chain reaction (FIG. 13A) for epoxides; in the case of epihalohydrins, an ether group is also formed but base is consumed upon halogenide replacement (FIG. 13B).

When the desired degree of completion of the reaction is obtained, the final polymer is either used directly or purified.

Purification

Purification of the final product from mobile, small molecule contaminants is challenging particularly for biomedical applications where very high levels of purity are required. Small molecule contaminants are the diepoxide, epihalohydrin or multifunctional epoxide/epihalohydrin molecules itself and various stereoisomers of the partially reactive, partially hydrolyzed intermediate products (FIG. 10). Of somewhat lower concern are the fully hydrolyzed products, since they are less reactive (FIG. 10). Nevertheless, their degradation and detoxification can still be a burden on target organisms or cells.

There are two main routes of purification: physical removal and chemical reaction. Established examples (WO2017076495A1) of physical removal are dialysis or the use of an adsorbing agent; chemical removal can be obtained through heating, addition of a catalyst, addition of a nucleophile, addition of water; combinations of various physical and chemical methods are possible (WO2017076495A1).

Physical Removal

Figure 15:
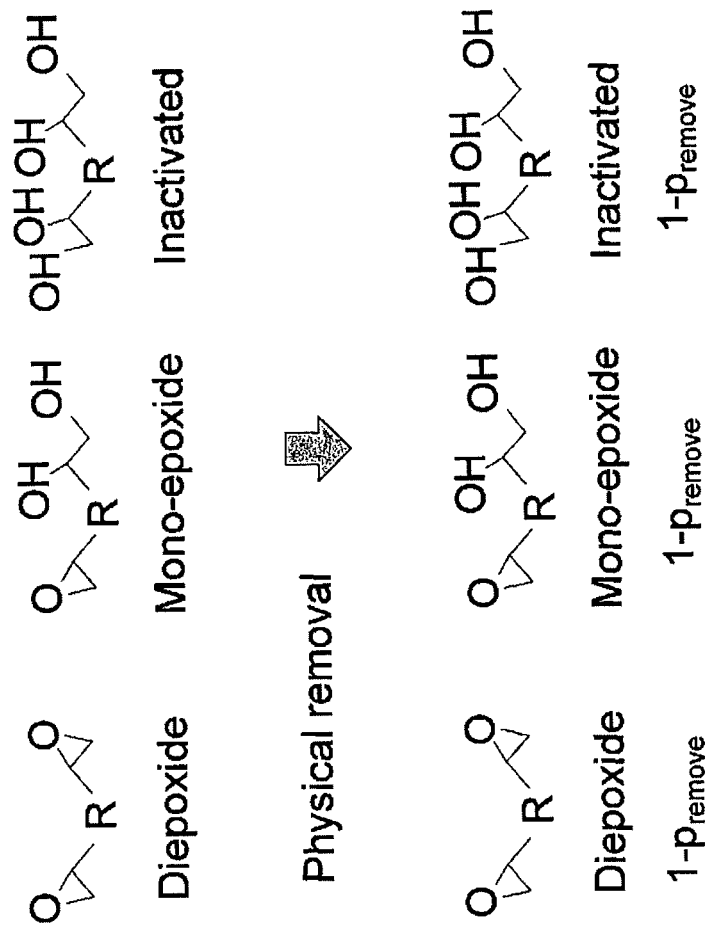
FIG. 15 shows physical removal.

Physical removal as shown in FIG. 15, to a first approximation, affects all mobile species similarly. This outlines the importance of an efficient physical removal method, for the mono-epoxide where the decay is slower (see chemical removal section), and particularly for the inactivated species, which under chemical inactivation accumulate. The spongy cake resulting from the lyophilization crosslinking process described here is particularly suitable for efficient washing, as it can rapidly be exposed to new washing solutions by exchange the pore fluid by compression cycles or steady flow through the pores. This in particular avoids the need for time-consuming and inefficient dialysis steps as required in the art for the purification of more homogeneous, less densely crosslinked hydrogels (e.g. WO2017076495A1).

Chemical Deactivation

Figure 14:
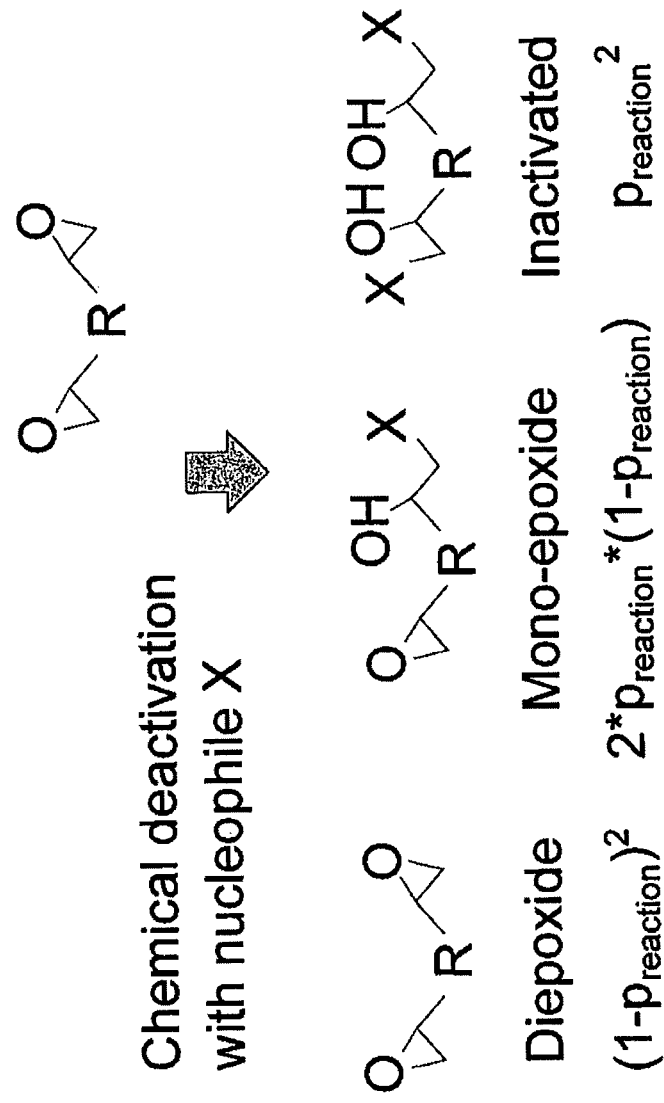
FIG. 14 represents chemical deactivation.

A main route of chemical deactivation is reaction with a nucleophile (H—)X; if X is water (H—OH), then this is the hydrolysis reaction as shown in FIG. 14.

Chemical deactivation converts reactive molecules into less reactive ones, but is unable to remove their inactivation products from the reaction mixture. For the case of multifunctional epoxide and epihalohydrin species, it converts molecular species with all or most reactive sites conserved to species with a lesser number of reactive groups, and it finally accumulates the fully deactivated species, which may still have residual toxicity.

Example Estimations for Chemical and Physical Deactivation in Existing Products

The diepoxide butanedioldiglycidyl ether in dermal filler products is required to be controlled to 2 ppm or below (De Boulle K, Glogau R, Kono T, Nathan M, Tezel A, Roca-Martinez J X, Paliwal S, Stroumpoulis D., Dermatol Surg. 2013 December; 39(12):1758-66), from an initial concentration on the order of about 1000 ppm in a typical reaction mixture. This indicates a reduction in concentration of at least a factor of 500, which includes in part the crosslinking process.

Under purely chemical purification, for a diepoxide molecule to persist, both epoxides groups must have failed to react, and so one calculates the individual probability of persistence for an epoxide group to be about sqrt(1/500) =4.5%. This implies that under purely chemical purification, even though the original diepoxide has nearly disappeared, rather large quantities of reactive epoxide groups can persist—in the form of mono-epoxides and pendant groups (1000 ppm butanedioldiglycidyl ether would be about 10 mM total epoxide, of which some 0.45 mM would remain). Under purely chemical deactivation, the fully hydrolyzed di-diol species accumulate and then present a toxicological load when implanted.

Under purely physical removal, one would expect the different impurities (diepoxide, various mono-epoxides, and di-diol isomers) to be roughly equally efficiently removed, although there might be slight differences arising from mobility and affinity to the crosslinked polymer. In a very optimistic scenario (negligeable production of mono-epoxide in the crosslinking process), under physical removal, one could indeed claim that total epoxide content would be below the equivalent of 2 ppm butanedioldiglycidyl ether (equivalent to 0.02 mM total epoxide).

In practice, chemical and physical removal have to be combined. Physical removal is more efficient at removing equally the various small molecule contaminants, whereas only chemical inactivation can inactivate bound chemical groups.

From the available data, one would judge that current removal techniques, and in particular the state of art techniques disclosed in WO2017076495A1 can at best guarantee a level of about 0.02 mM remaining epoxide, and possibly substantially more since only the free diepoxide is measured.

Inactivation of Pendant Epoxide

In some applications, such as modification of the crosslinked structure by nucleophiles, the pendant epoxide groups (FIG. 11, FIG. 9) are a desired feature. In other applications, particularly in implants, their residual toxicity due to their reactivity towards proteins, nucleic acids and other nucleophiles is of concern and they should be inactivated.

As the pendant epoxides are bound to the crosslinked polymer structure, only chemical inactivation is possible.

DETAILED DESCRIPTION OF THE INVENTION

The following examples clarify the invention further in more detail.

A) Manufacture of the Composition

Example 1 a) Sodium carboxymethylcellulose (1.5% in mass, degree of substitution 0.8) and butanedioldiglycidyl ether BDDE (0.14% in mass) were dissolved in 15 mM tetrapropylammonium hydroxide solution;
b) the solution was poured into a clean recipient having an aspect ratio of 1/10 and the system was placed at −20° C. during 2 hours;
c) the solution was lyophilized using the following parameters: temperature: −20° C., pressure: 100 mTorr; and
d) the lyophilized product obtained in step c) was heated in a hermetically closed container during 3 hours at 80° C.

The remaining reactive epoxide was titrated by complete reaction with sodium thiosulfate in a neutral phosphate buffer (Bunte salt reaction), followed by back titration of the remaining thiosulfate with iodine and starch indicator. We found the following total epoxide concentrations (free and bound) after various steps:

after step b) and thawing 14.0 mM (101% of initial)
after step c) with dissolution to restore the original volume 14.1 mM (102% of initial)
after step d) with suspension to restore the original volume 0.98 mM (7% of initial)

Given the high rate of conversion (93% of the epoxide), there is nearly only double-bound BDDE (>90%) and single-bound BDDE (<10%). Nearly no change in mechanical properties (Young modulus) occurs upon incubation with NaOH, so the bonds are ether bonds, not ester bonds. Confocal microscopy reveals highly concentrated walls, occupying a wall fraction of about 4%. From this, the concentration of carboxymethylcellulose within the walls is about 40%. The swelling ratio given by wet to dry weight would then be about 2.5 for the wall material. This is an extremely low value, typical dermal fillers have concentrations of hyaluronic acid in the few percent range and swell if given the possibility, so that their swelling ratio is on the order of 100.

This allows the conclusion that most double crosslinked BDDE molecules provide actual, efficient crosslinks. Assuming a ⅔ effective crosslinking efficiency, we get:

Resulting $N_1$=0.6 and Resulting $N_2$=0.4; and therefor $$N_1 > 0.55*(N_1+N_2)$$

Example 2 a) Sodium alginate (1% in mass, degree of substitution 0.8) and butanedioldiglycidyl ether BDDE (0.1% in mass) were dissolved in 7.5 mM sodium hydroxide solution;
b) The solution was poured into a clean recipient having an aspect ratio of 1/10 and the system was placed at −20° C. during 2 hours;
c) the solution was lyophilized using the following parameters: temperature: −5° C., pressure: 50 mTorr;
d) the lyophilized product obtained in step c) was heated in a hermetically closed container during 14 hours at 80° C.

The remaining reactive epoxide was titrated by complete reaction with sodium thiosulfate in a neutral phosphate buffer (Bunte salt reaction), followed by back titration of the remaining thiosulfate with iodine and starch indicator. We found the following total epoxide concentrations (free and bound) after various steps:

after step d) with suspension to restore the original volume 0.72 mM (5% of initial) Resulting $N_1$=0.45 and Resulting $N_2$=0.55; and therefore $$N_1 > 0.4*(N_1+N_2)$$

Example 3 a) Hyaluronic acid (1% in mass) and diglycidylether (0.1% in mass) was dissolved in water with a catalyst (Tetramethylammoniumhydroxide at a concentration of 5 mM);
b) the solution was poured into a clean recipient having an aspect ratio of 1/10 and place the system at −80° C. during 2 hours;
c) the solution was lyophilized using the following parameters: temperature: −20° C., pressure: 500 mTorr; and
d) the lyophilized product was heated obtained in step c) during 2 hours at 100° C.

Resulting $N_1$=0.41 and Resulting $N_2$=0.59; and therefore $$N_1 > 0.4*(N_1+N_2)$$

Example 4 a) Hyaluronic acid (4% in mass) and the substituted epichlorohydrin derivative 2-(Chloromethyl)-2-Cyclohexyloxirane (0.2% in mass) was dissolved in water with a catalyst (NaOH at a concentration of 5 mM);
b) the solution was poured into a clean recipient having an aspect ratio of 1/10 and the system was placed at −20° C. during 2 hours;
c) the solution was lyophilized using the following parameters: temperature: −20° C., pressure:500 mTorr; and
d) the lyophilized product obtained in step c) was heated during 2 hours at 80° C.

Resulting $N_1$=0.36 and Resulting $N_2$=0.64; and therefore $$N_1 > 0.35*(N_1+N_2)$$

Example 5 a) Polyvinylalcohol (10% in mass) and 4-arm PEG (2 kDa MW, terminated with an epoxide group on each arm, 1%) was dissolved in water with a catalyst (NaOH, 20 mM);

b) the solution was poured into a clean recipient having an aspect ratio of 1/2 and the system was placed at −30° C. during 12 hours;
c) the solution was lyophilized using the following parameters: temperature: −30° C., pressure: 1 Torr; and
d) the lyophilized product obtained in step c) was heated during 4 hours at 80° C.

Resulting $N_1$=0.36 and Resulting $N_2$=0.64; and therefore $$N_1 > 0.35*(N_1+N_2)$$

Example 6 a) Sodium carboxymethylcellulose (1.5% in mass, degree of substitution 0.8), butanedioldiglycidyl ether BODE (0.5% in mass) and diglycidylether (0.5% in mass) were dissolved in 15 mM tetrapropylammonium hydroxide solution;
b) the solution was poured into a clean recipient having an aspect ratio of 1/10 and the system was placed at −20° C. during 2 hours;
c) the solution was lyophilized using the following parameters: temperature: −20° C., pressure: 100 mTorr; and
d) the lyophilized product obtained in step c) was heated in a hermetically closed container during 3 hours at 80° C.

Resulting $N_1$=0.6 and Resulting $N_2$=0.4; and therefore $$N_1 > 0.55*(N_1+N_2)$$

B) Fragmentation of the Composition

Example 7

The products obtained in examples 1 to 6 were subjected to a further step consisting in fractioning the scaffold (i.e. of the single polymeric molecule) obtained. For this, a bulk scaffold or a bulk scaffold piece (as obtained in examples 1 to 6) was placed in a plastic bag and compressed and sheared manually to create the particles according to the invention.

Example 8

In another embodiment, the bulk scaffold from examples 1 to 6 was hydrated and extruded through a thin tubular element by applying a known pressure to obtain a fragmented material. The particle size was controlled by the pressure applied on the piston of the syringe and by the size of the extruding cannula. Typically, a pressure of 15 bars and a cannula of 14 G was used, but by suitable adaptation of the pressure extrusion through much larger and smaller gauges (up to Gauge 32 G) can also be obtained.

C) Purification of the Composition

Example 9

The composition after manufacture (examples 1-6) or fragmentation (examples 7-8) is typically an insoluble sponge or multitude of sponge particles that can be spontaneously hydrated upon contact with a solvent (and in particular, aqueous solutions and solvent mixtures containing a sizeable fraction of water). Upon application of vacuum or decreased pressure through a filter membrane, the hydrated or solvent-swollen composite rapidly loses pore fluid. It can readily be rehydrated due to its elastic recoil properties and affinity for the solvent.

10 g of the composition obtained by way of one of the examples 1 to 6 were placed on top of a filter membrane to which vacuum was applied from below. The corn position was hydrated with 500 mL of physiological saline solution (0.9% NaCl in water). After 1 min vacuum was applied from below to the filter membrane. After 10 minutes the composition had lost most of its pore fluid and hydration water. The procedure was repeated three times. The composition was placed in 2M NaOH for 24 h at 40° C., and washed another 7× with NaCl 0.9% as described above.

Carrying out the purification given in this example 9 on the composition produced by example 1, followed by fragmentation via the example 8, by HPLC and mass spectroscopy, the detected amount of butanedioldiglycidylether (BDDE) was below the quantification limit of our method (0.3 ppb); the total amount of free monohydrolysed BDDE derivatives was also below the quantification limit of 0.3 ppb.

D) Analysis of Crosslinking

Analysis Method 1: Chemical Polysaccharide Degradation

The analysis of crosslinked polysaccharide compositions is usually done by complete degradation of the polysaccharide backbone under conditions which preserve the crosslinker. A concrete workable method is given in Holmberg et al., Carbohydrate Research 272 (1995) 203-2011, where acid hydrolysis is used to completely degrade the polysaccharide strands in the covalently crosslinked, purified polymer while sparing the ether crosslinks and pendant groups. Thereafter, permethylation and gas chromatography/mass spectroscopy are used to identify the various fragments resulting from crosslinking and pendant modification. For each detected fragment, the relative molar amount incorporated of crosslinker can be determined from stoichiometric and detection sensitivity considerations; the structure of the fragments and most notably the number of glucide units bound allow to estimate the number of actual crosslinks per crosslinker molecule as shown in Table 1 for the data by Holmberg et al. From this, the average number of effective crosslinks per crosslinker molecule can be compared to the possible number of crosslinks per crosslinker molecule as done in the example equation eq. 12 and eq. 13, and more generally as prescribed by eq. 8 and eq. 4.

Analysis Method 2: Enzymatic Polysaccharide Degradation

Similar to method 1, enzymatic degradation can be used to degrade the polysaccharide strands. This requires the availability of an enzyme capable of degrading the polysaccharide strands even in the presence of the crosslinks. Such enzymes are typically known for hyaluronic acid based formulations (see Kablik, J., G. D. Monheit, L. Yu, G. Chang, and J. Gershkovich; Comparative physical properties of hyaluronic acid dermal fillers. Dermatol Surg, 2009. 35 Suppl 1: p. 302-12.). Thereafter, chromatographic techniques (HPLC in Kablik et al.) are used similarly than in Analysis Method 1, followed by similar calculations.

E) Manufacture of an Implantable Tissue Engineering Material Comprising the Composition According to the Invention Example 10

A mass of 10 g of the composition obtained by one of the examples 1-6 (in the form of a scaffold), followed by fragmentation via examples 7 or 8, and purified as described in example 9 was rinsed in 100 mL of NaOH 5M. The scaffold was then incubated during 20 minutes at room temperature under mild agitation. The NaOH solution was replaced by 100 mL of LAL water and left incubating for 20 minutes. This step was repeated three times. The last rinsing step was performed by replacing LAL water by 100 mL of PBS. After the rinsing procedure, the polymer concentration was adapted to target by aspirating or adding PBS. In the case of aspirating, the scaffold was placed on a filter device and PBS was removed by applying suction through the filter.

The resulting scaffold was then poured directly in sterile syringes. The closed syringes were then inserted into a blister packaging which was sealed hermetically, and finally sterilized by steam using a temperature of 121° C. applied during 20 minutes.

Example 11

A scaffold was cut out from a composition as obtained in one of the examples 1-6, optionally purified via example 9, using a sharp clean blade or a laser cutter to the desired shape of the implant. A rectangular scaffold of 10 mm×10 mm×3 mm having a mass of 10 g of the scaffold with the composition was rinsed in 100 mL of NaOH 5M. The scaffold was incubated during 20 minutes at room temperature under mild agitation. The NaOH solution was replaced by 100 mL of LAL water, left incubating for 20 minutes. This step was repeated three times. The last rinsing step was performed by replacing LAL water by 100 mL of PBS. The rectangular scaffold was then inserted into a sterile and clean blister packaging, sealed hermetically and sterilized using steam sterilization, using a cycle of 30 minutes at a temperature of 121° C.

F) Clinical Use of the Composition According to the Invention

Indication: reconstruction or enhancement of soft tissue volumes (plastic surgery).

Example of indications requiring soft tissue volume reconstruction or enhancement:
  Breast reconstruction after mastectomy, as a stand-alone solution or in combination with silicone implants or with FLAPs, breast reconstruction after tumorectomy, correction of tuberous breast, enhancement of breast volume;
  Body contouring, correction of deformities acquired through liposuction, correction of pectus excavatum.

For all those indications:

Prior the intervention, the surgeon using the soft tissue engineering material defines the areas where new volumes were needed. For this, the volume defects was visually evaluated and lines were traced using a marker defining the future injection lines, Alternatively, a 3D imaging system was used to record the volume before the intervention and help the surgeon to plan the intervention.

During the intervention performed following aseptic procedures, the area of skin where injections will be performed are rigorously disinfected (for example betadine). A dose of local anesthetics is injected subcutaneously (example: Lidocaine 10 mg/mL). After a few minutes, the surgeon can proceed to the injection of the composition. The sterile blister packaging containing the syringe containing the composition according to the invention is unpacked, the syringe cap is unscrewed and a blunt tip cannula is connected, while maintaining aseptic conditions. Adjustment for dead volume is performed extruding a small amount of product to remove air contained in the cannula in order to avoid injecting air in the patient. A small incision using a trocar 16 G is performed and the cannula is inserted through the disinfected skin. Once the position of the tip of the cannula reaches the desired position, the composition of the invention is injected in the subcutaneous adipose tissue layer in a retrograde movement. The incision site can be closed with a small stitch.

Possibly, several injection sessions can be performed in a subsequent procedure, in order to re adjust the volume, the shape or to further increase the volume.

The injection procedure or the placement procedure can be performed while monitoring the injection plane/depth using an ultrasound device. It enables a precise injection.

Face Enhancement or Reconstruction after Moh Surgery

The composition of the invention is packaged in a 1 mL sterile syringe. A thin cannula or needle is connected to the syringe and the composition of the invention is injected subcutaneously, or intra-cutaneous.

Clinical use of the composition of the invention to reinforce organ's walls:

Heart: The composition of the invention is distributed through a tubular element (catheter, syringe, endoscope, . . . ) on the surface of the heart to create a mechanical reinforcement where a weakness exists. Potentially, adequate cells can be mixed with the composition of the invention prior or during the in situ application. The cells can also be culture primarily to the in situ deposition.

Note: the scaffold made out of the composition of the invention is used to protect the grafted cells and increase their chances to participate to the reconstruction or regeneration process in vivo.

Brain: The composition of the invention is injected through a tubular element using a stereotaxic frame in the brain in order to compensate for a volume loss following tumorectomy, congenital deformity, stroke.

Potentially, the composition is mixed with neural cells during or prior or after the injection of the composition of the invention. Cells can be cultured/differentiated before or during or after the in, vivo procedure.

Note: the scaffold made out of the composition of the invention is used to protect the grafted cells and increase their chances to participate to the reconstruction or regeneration process in vivo.

Bone Marrow:

Bone marrow cells are cultured in or on the top of a scaffold material made out of the composition of the invention. The cell culture can be done priory or during the injection or, application of the composition of the present invention in situ, in the bone marrow, where a lesion has been evidenced.

G) Clinical Results Obtained and Comparative Studies with Prior Art Materials

In the following figures, the term "EPI scaffold" refers to the scaffold having the composition of the invention. It stands for "Elastic Porous Injectable" scaffold.

Figure 16:
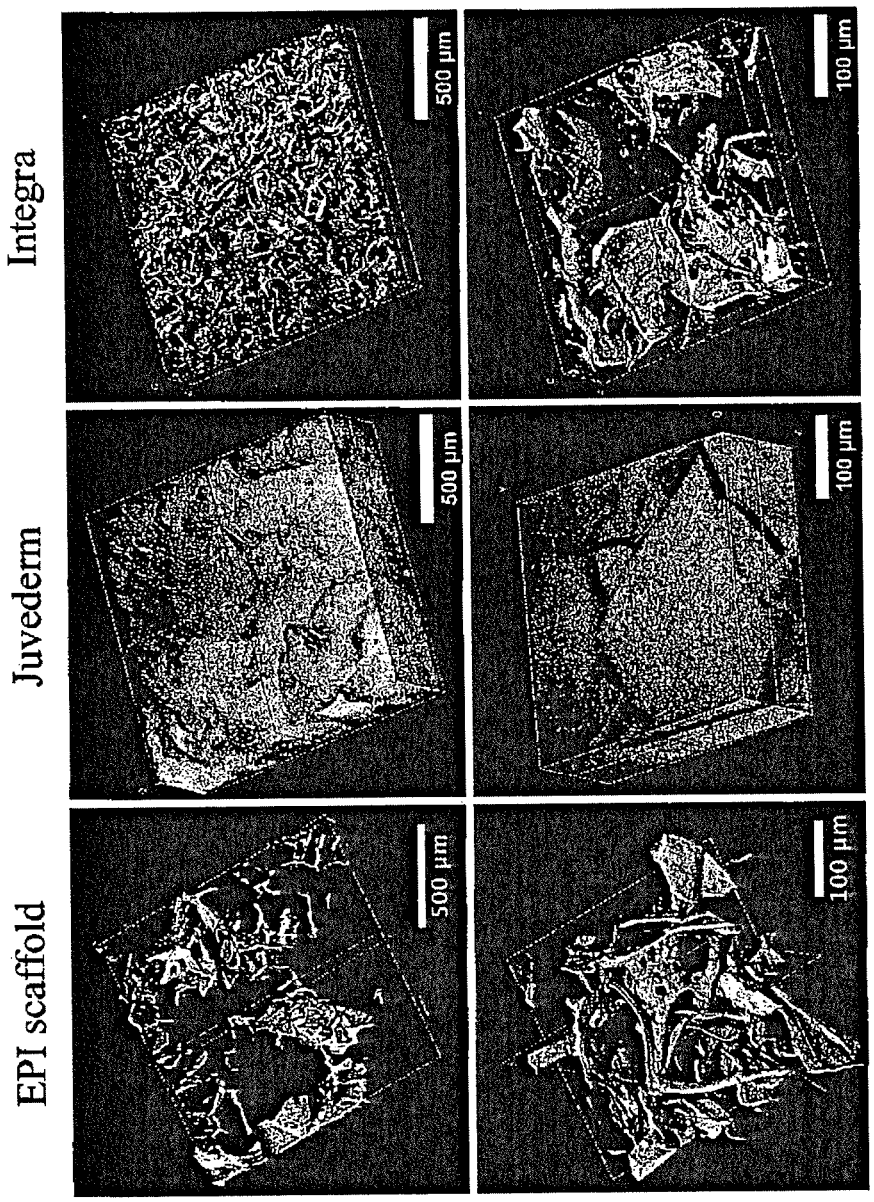
FIG. 16 shows the structure of the composition according to the invention compared to prior art materials.

As shown in FIG. 16 the structure of the composition according to the invention (EPI scaffold) is compared to two commercially available biomaterials ("Juvederm" of Allergan and "Integra" of Integra Lifesciences) using SEM images and confocal images (low and high magnification, second and third row respectively) of the three different categories of biomaterials.

Figure 17:
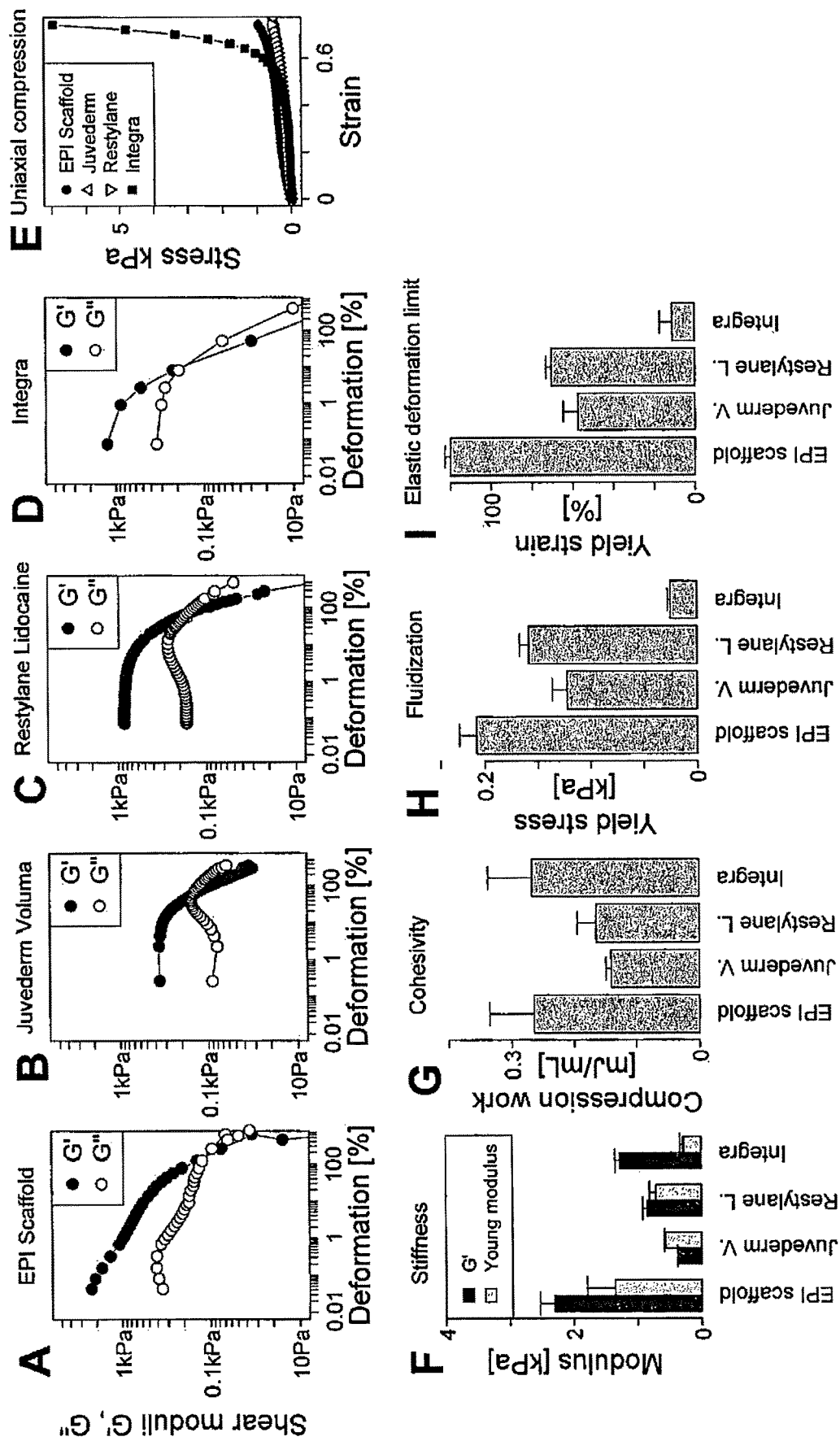
FIG. 17 shows the mechanical characterization compared to prior art materials.

In FIG. 17 the composition according to the invention (EPI scaffold) is further characterized by its mechanical properties. A), B), C) Evaluation of elastic storage modulus G' and viscous loss modulus G" by oscillatory shear rheology. Data acquired for A) the EPI scaffold, B) a commercial sample of Juvederm Voluma and C) Restylane Lidocaine D) a fragmented sample of Integra collagen matrix. Oscillatory shear excitation at 0.2 Hz at increasing stress; reported are the associated measured deformation, G' and G" values. E) Uniaxial compression of the three materials. F) Comparison of the material stiffness values (G' in shear, Young modulus in uniaxial compression). G) Cohesivity as quantified by the work required for 70% uniaxial compression. H) Yield stress indicating the minimal force for fluidization. I) Yield strain as the upper deformation limit before fluidization. The material produced by the teaching of this invention approximately matches commercial materials at high deformation and thus has similar injectability characteristics. Its special structure obtained by efficient crosslinking imparts, however, stronger, more elastic properties at low deformation, important for shape stability and tissue ingrowth.

Figure 18:
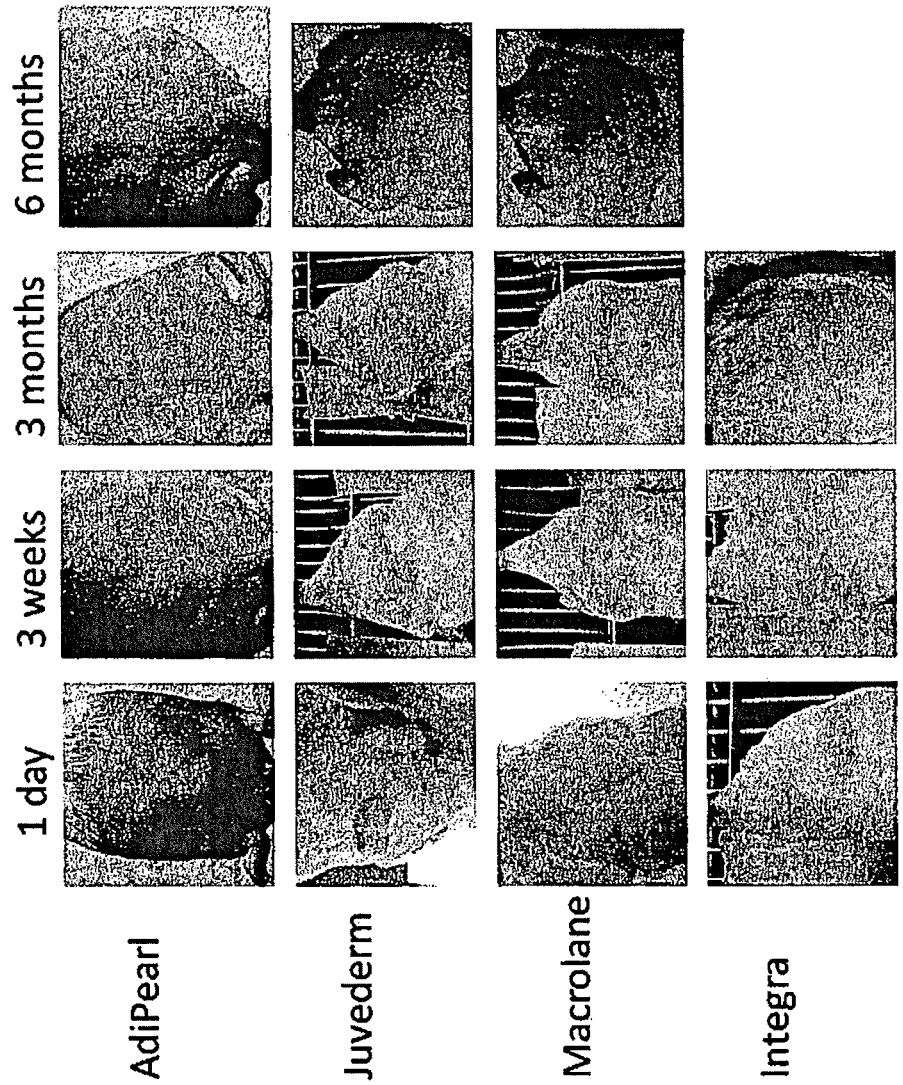

FIG. 18 shows representative macroscopic pictures of mice injected with the different tested materials. Pictures of injected mice at 1 day, 3 weeks, 3 months and 6 months after the injection procedure. The samples can be seen in the back of the animal on the two side of the flank. EPI scaffold (a1-a4) and Macrolane samples (c1-c4) were stable during the study, whereas Juvederm samples (b1-b4) swelled 3 weeks after the injection procedure before being almost entirely degraded at 6 months. Integra samples (d1-d3) degraded within few weeks (d3: no sample visible, d4: the study was stopped due to full degradation of the material).

FIG. 19 represents macroscopic pictures of explanted samples of different materials. Images of the explanted materials 3 months (a1-d1) and 6 months (a2-d2) post-injection. Integra study was stopped after 3 months due to its complete degradation. Implants are shown with a white dashed line. Scale bar is 0.5 cm.

FIG. 20 shows representative H&E pictures of the different tested items. Images of EPI scaffold from 3 weeks post injection to 6 months (a1-a3). Images of Juvederm and Macrolane, respectively (b1-b3) and (c1-c3), at 3 weeks, 3 months and 6 months after the injection. Images of Integra material after 3 weeks (d1) and after 3 months (d2) where a minimum amount is still visible. Scale bar is 250 μm.

The invention claimed is:

1. A composition comprising a polyol crosslinked with
   a) a multifunctional epoxide; or
   b) an epihalohydrin; or
   c) a molecule or crosslinker mixture comprising multiple epihalohydrin and/or epoxide groups or molecules;
   wherein the composition
      has a number $N_1$ of effective ether crosslinks per crosslinker molecule as calculated by subtracting 1 from the average number of distinct polyol repeat units bound per crosslinker molecule,
      the remaining reactive groups on the crosslinker are ineffective in crosslinking and provide a number $N_2$ of pendant groups per crosslinker molecule,
      among the $N_2$ groups per crosslinker there are $N_3$ groups per crosslinker that are unreacted or otherwise retain reactivity against nucleophiles,
   wherein the relationship between $N_1$ and $N_2$ is: $N_1 > 0.35 (N_1+N_2)$, and
   wherein
   A) the composition comprises a multitude of interconnected pores;
   B) the composition is characterized by a structure comprising a multitude of individual sponge particles; and
   C) the particles have a number of protrusions at their surfaces.

2. The composition of claim 1, wherein the polyol is a negatively charged polysaccharide, polyvinyl alcohol, polyethylene glycol (PEG), or a mixture thereof.

3. The composition of claim 1, wherein the multi-functional epoxide is a di-epoxide.

4. The composition of claim 1, wherein the concentration of the $N_3$ ether groups with a reactive epoxy group is below 5 micromoles/kg of dry mass of the composition.

5. The composition of claim 1, wherein the concentration of the $N_3$ ether groups with a reactive epoxy group is above 50 micromoles/kg of dry mass of the composition.

6. The composition of claim 3, wherein the concentration of soluble free di-epoxide species in the composition is lower than 100 nanomoles/g of dry weight of the composition.

7. The composition of claim 1, wherein the concentration of soluble free mono-epoxide species in the composition is lower than 2000 nanomoles/g of dry weight of the composition.

8. The composition of claim 1, wherein the total concentration of leachable molecules with epoxide or halogen functionalities is below 200 ppb.

9. A method for producing the composition of claim 1 comprising:
   A) dissolving a polyol and a multifunctional epoxide; an epihalohydrin; or a molecule comprising multiple epihalohydrin and/or epoxide groups; or a combination thereof in a solvent to form a solution;
   B) cooling the solution to a temperature below the crystallization point of the solvent to form an at least partially frozen solution; and
   C) lyophilizing the at least partially frozen solution, so that after the lyophilization of step C) at least 50% of the originally present epoxide groups remain present in the product obtained; or
   C') thawing the at least partially frozen solution obtained in step B).

10. The composition of claim 3, wherein the di-epoxide is ethylene glycol-diglycidyl ether or butanediol-diglycidyl ether.

11. The composition of claim 1, wherein the relative amount of doubly crosslinked hydroxide groups in the polyol compared to the total amount of reactive hydroxyl groups before crosslinking of the polyol is between 0.1% and 10%.

12. The composition of claim 1, wherein the polyol is a molecule having at least two hydroxyl groups.

13. The composition of claim 1, wherein the polyol is a carbohydrate or an anionic carbohydrate.

14. The method of claim 9, wherein the multi-functional epoxide is a di-epoxide.

15. The method of claim 14, wherein the di-epoxide is ethylene glycol-diglycidyl ether or butanediol-diglycidyl ether.

16. The method of claim 9, wherein the composition obtained after step D is fragmented, before being purified by repeated washing cycles induced by addition of washing solution followed by removal of washing solution by application of a suitable pressure differential to the composition placed on a mesh or filter membrane.

17. The composition of claim 2, wherein the multi-functional epoxide is a di-epoxide.

18. The composition of claim 17, wherein the di-epoxide is ethylene glycol-diglycidyl ether or butanediol-diglycidyl ether.

19. The composition of claim 2, wherein the total concentration of leachable molecules with epoxide or halogen functionalities is below 200 ppb.

20. The composition of claim 2, wherein the polysaccharide is (i) an alginate; (ii) hyaluronic acid; or (iii) a carboxymethylcellulose.

21. The method of claim 9, wherein the epihalohydrin is epichlorohydrin, (chloromethyl)-2-cyclohexyloxirane, or 5-chloro-pentane-1,2-epoxide or a combination thereof.

22. The method of claim 9, further comprising following step C) or step C'), wherein a step D) comprises heating the lyophilized product obtained in step C) or the thawed product obtained in step C').

23. The method of claim 9, further comprising following step C) or step C'),
sterilizing the composition.

24. The method of claim 9, wherein step C) or step C') is performed at least 2 hours after step B).

25. The method of claim 9, wherein the composition obtained after step C) or C') is fragmented, before being purified by repeating washing cycles induced by addition of washing solution followed by removal of washing solution by application of a suitable pressure differential to the composition placed on a mesh or filter membrane.

* * * * *